US009006447B2

(12) United States Patent
Koerber et al.

(10) Patent No.: US 9,006,447 B2
(45) Date of Patent: Apr. 14, 2015

(54) METHOD FOR PREPARING SUBSTITUTED ISOXAZOLINE COMPOUNDS AND THEIR PRECURSORS 4-CHLORO, 4-BROMO- OR 4-IODOBENZALDEHYDE OXIMES

(75) Inventors: Karsten Koerber, Eppelheim (DE); Markus Kordes, Bobenheim-Roxheim (DE); Michael Rack, Eppelheim (DE); Wolfgang Von Deyn, Neustadt (DE); Florian Kaiser, Mannheim (DE)

(73) Assignee: BASF SE, Ludwigshafen (DE)

( * ) Notice: Subject to any disclaimer, the term of this patent is extended or adjusted under 35 U.S.C. 154(b) by 166 days.

(21) Appl. No.: 13/883,149

(22) PCT Filed: Oct. 31, 2011

(86) PCT No.: PCT/EP2011/069072
§ 371 (c)(1),
(2), (4) Date: May 2, 2013

(87) PCT Pub. No.: WO2012/059441
PCT Pub. Date: May 10, 2012

(65) Prior Publication Data
US 2013/0225826 A1 Aug. 29, 2013

Related U.S. Application Data

(60) Provisional application No. 61/409,604, filed on Nov. 3, 2010.

(30) Foreign Application Priority Data

Nov. 3, 2010 (EP) ..................... 10189896

(51) Int. Cl.
C07D 261/04 (2006.01)
C07D 413/12 (2006.01)
C07C 249/12 (2006.01)
C07C 251/48 (2006.01)

(52) U.S. Cl.
CPC ............ *C07D 261/04* (2013.01); *C07C 249/12* (2013.01); *C07D 413/12* (2013.01)

(58) Field of Classification Search
None
See application file for complete search history.

(56) References Cited

U.S. PATENT DOCUMENTS

| | | | |
|---|---|---|---|
| 2007/0066617 A1 | 3/2007 | Mita et al. | |
| 2009/0023923 A1 | 1/2009 | Mizukoshi et al. | |
| 2010/0137612 A1 | 6/2010 | Yaosaka et al. | |
| 2010/0144797 A1 | 6/2010 | Mita et al. | |
| 2010/0174094 A1 | 7/2010 | Zierke et al. | |
| 2011/0144349 A1 | 6/2011 | Kousaka et al. | |
| 2011/0172414 A1 | 7/2011 | Mita et al. | |
| 2011/0251398 A1 | 10/2011 | Mita et al. | |

FOREIGN PATENT DOCUMENTS

| | | |
|---|---|---|
| JP | 2007016017 | 1/2007 |
| JP | 2007106756 | 4/2007 |
| JP | 2008133242 | 6/2008 |
| JP | 2008156347 | 7/2008 |
| JP | 2008239611 | 10/2008 |
| WO | WO 2005085216 | 9/2005 |
| WO | WO 2007026965 | 3/2007 |
| WO | WO 2007070606 | 6/2007 |
| WO | WO 2007074789 | 7/2007 |
| WO | WO 2007075459 | 7/2007 |
| WO | WO 2007079162 | 7/2007 |
| WO | WO 2007105814 | 9/2007 |
| WO | WO 2007125984 | 11/2007 |
| WO | WO 2008012027 | 1/2008 |
| WO | WO 2008019760 | 2/2008 |
| WO | WO 2008108448 | 9/2008 |
| WO | WO 2008122375 | 10/2008 |
| WO | WO 2008130651 | 10/2008 |
| WO | WO 2008145740 | 12/2008 |
| WO | WO 2008150393 | 12/2008 |
| WO | WO 2008154528 | 12/2008 |
| WO | WO 2009001942 | 12/2008 |
| WO | WO 2009002809 | 12/2008 |
| WO | WO 2009003075 | 12/2008 |
| WO | WO 2009024541 | 2/2009 |
| WO | WO 2009049846 | 4/2009 |
| WO | WO 2009063910 | 5/2009 |
| WO | WO 2009126668 | 10/2009 |
| WO | WO 2009142569 | 11/2009 |
| WO | WO 2010003877 | 1/2010 |
| WO | WO 2010003923 | 1/2010 |
| WO | WO 2010005048 | 1/2010 |
| WO | WO 2010072781 | 7/2010 |
| WO | WO 2010125130 | 11/2010 |
| WO | WO 2011161130 | 12/2011 |
| WO | WO 2012151512 | 11/2012 |

OTHER PUBLICATIONS

Barnard, Christopher, F.J., "Carbonylation of Aryl Halides: Extending the Scope of the Reaction", Organic Process Research & Deveopment, 2008, p. 566-574, vol. 12.

Fontán, Noelia, et al. "A conjunctive diiodoheptaene for the synthesis of C2-symmetirc carotenoids", Chem Commun., 2013, p. 2964-2996, vol. 49, including Electronic Supplementary Material (ESI) for Chemical Communications.

Ulrich, Gilles, et al. "Carbonyl derivatives of Boradiazaindacene viacatalytic CO insertion", Journal of Organic Chemistry, 2012, p. 5036-5048, vol. 77.

(Continued)

Primary Examiner — Kamal Saeed
(74) Attorney, Agent, or Firm — Brinks Gilson & Lione

(57) ABSTRACT

The present invention relates to a method for preparing 4-chloro-, 4-bromo- or 4-iodobenzaldehyde oximes and phenyl-substituted isoxazoline compounds prepared from these oximes.

29 Claims, No Drawings

(56) References Cited

OTHER PUBLICATIONS

Schoenberg et al., "Palladium-Catalyzed Amidation of Aryl, Hereocyclic and Vinylic Halides," J. Org. Chem., vol. 39, (1974), pp. 3327-3331.

Dorwald, "Side Reactions in Organic Synthesis," eds. Wiley, 2005, pp. 1-15, 279-308.

Hatanaka et al., "An Improved Synthesis of 4-[3-(Trifluoromethyl)-3H-Diazirin-3-YL]Benzoic Acid for Photoaffinity Labeling", Heterocycles, vol. 35, No. 2, (1993), pp. 997-1004.

Nader et al., "A Novel Fluoride Ion Mediated Olefination of Electron-Deficient Aryl Ketones by Alkanesulfonyl Halides", J. Org. Chem. vol. 59, (1994), pp. 2898-2901.

Doamaral et al., "AntiMalarial Activity of Guanyl Hydrazone Salts of Aromatic Ketones Part 2 Development of Active Poly Halo Derivatives," Journal of Medicinal Chemistry, vol. 14, No. 9, (1971), pp. 862-866.

Beech, "Preparation of Aromatic Aldehydes and Ketones from Diazonium Salts," Journal of the Chemical Society, (1954), pp. 1297-1302.

Jolad et al., "2-bromo-4-methylbenzaldehyde (p-tolualdehyde, 2-bromo-)," Organic Synthesis—Collective Volumes, eds. John Wiley and Sons, vol. 46, (1966), pp. 13-16.

International Search Report, issued in PCT/EP2011/069072, dated Jun. 1, 2012.

International Preliminary Report on Patentability, issued in PCT/EP2011/069072, dated Feb. 28, 2013.

METHOD FOR PREPARING SUBSTITUTED ISOXAZOLINE COMPOUNDS AND THEIR PRECURSORS 4-CHLORO, 4-BROMO- OR 4-IODOBENZALDEHYDE OXIMES

This application is a National Stage application of International Application No. PCT/EP2011/069072, filed Oct. 31, 2011, which claims the benefit of U.S. Provisional Application No. 61/409,604 filed Nov. 3, 2010, the entire contents of which are hereby incorporated herein by reference. This application also claims priority under 35 U.S.C. §119 to European Patent Application No. 10189896.3 filed Nov. 3, 2010, the entire contents of which is hereby incorporated herein by reference.

DESCRIPTION

The present invention relates to a method for preparing 4-chloro-, 4-bromo- or 4-iodobenzaldehyde oximes and phenyl-substituted isoxazoline compounds prepared from these oximes.

Because of their pesticidal activity, substituted isoxazolines are of great interest especially as pesticides, and as precursors of such active ingredients. For their synthesis, a series of methods comprising several organometallic steps is available. However, organometallic methods are afflicted by some disadvantages. For instance, their attractiveness is reduced by high costs, especially in the case of palladium-catalyzed reactions, lack of environmental compatibility, as in the case of nickel, and low maturity, especially in the case of catalysis with cobalt and iron compounds.

Accordingly there is an ongoing need to provide further methods of preparation of such substituted isoxazoline compounds having improved characteristics in comparison to prior art processes, such as a higher safety, reduced environmental impact and reduced production costs.

EP-A-1932836 relates to phenyl- or hetaryl-substituted isoxazolines and methods for producing them. The isoxazoline ring is generated in a ring-closing reaction in which a halogenated benzaldehyd oxime is reacted with a styrene compound (scheme 6). The oxime is prepared from the corresponding benzaldehyde by reaction with hydroxylamine (scheme 2), and the benzaldehyde is in turn prepared from a bromo, iodo or sulfonyloxy benzene by reacting this in a CO insertion reaction with CO in the presence of a hydride source, such as formic acid, and a transition metal catalyst, such as palladium (scheme 7).

It was an object of the present invention to provide an easily performable process for preparing 4-chloro-, 4-bromo- or 4-iodobenzaldehyde oximes and phenyl-substituted isoxazolines which in turn are prepared from such 4-chloro-, 4-bromo- or 4-iodobenzaldehyde oximes. This process should additionally be performable inexpensively and avoid or reduce the use of expensive organometallic reagents, especially of transition metal catalysts.

The object is achieved by the processes described in detail below.

The present invention provides a method for preparing oxime compounds of formula I

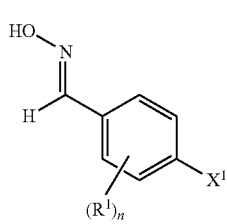

(I)

wherein
each $R^1$ is independently selected from F, Cl, CN, $NO_2$, $SF_5$, $C_1$-$C_6$-alkyl, $C_1$-$C_6$-haloalkyl, $C_3$-$C_8$-cycloalkyl, $C_3$-$C_8$-halocycloalkyl, $C_3$-$C_8$-cycloalkyl-$C_1$-$C_4$-alkyl, $C_3$-$C_8$-halocycloalkyl-$C_1$-$C_4$-alkyl, $C_1$-$C_6$-alkoxy, $C_1$-$C_6$-haloalkoxy, $C_1$-$C_4$-alkyl, $C_3$-$C_8$-cycloalkoxy, phenyl and a 3-, 4-, 5-, 6- or 7-membered saturated, partially unsaturated or completely unsaturated heterocyclic ring with 1, 2 or 3 heteroatoms or heteroatom groups selected from N, O, S, NO, SO and $SO_2$, as ring members, where phenyl or the heterocyclic ring may carry 1, 2 or 3 substituents selected from F, Cl, CN, $NO_2$, $SF_5$, $C_1$-$C_6$-alkyl, $C_1$-$C_6$-haloalkyl, $C_3$-$C_8$-cycloalkyl, $C_3$-$C_8$-halocycloalkyl, $C_3$-$C_8$-cycloalkyl-$C_1$-$C_4$-alkyl, $C_3$-$C_8$-halocycloalkyl-$C_1$-$C_4$-alkyl, $C_1$-$C_6$-alkoxy, $C_1$-$C_6$-haloalkoxy and $C_1$-$C_4$-alkoxy-$C_1$-$C_4$-alkyl;
$X^1$ is selected from Br and I and, in case that $R^1$ is not Cl or phenyl which carries one or more substituents F or Cl or a heterocyclic ring which carries one or more substituents F or Cl, may also be Cl; and
n is 1 or 2;
which method comprises following steps:
(i) reacting an aniline compound of formula II

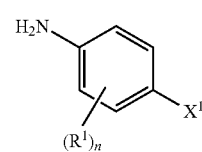

(II)

wherein n and $X^1$ are as defined above,
with a nitrite salt in an acidic medium to a diazonium salt; and
(ii) reacting the diazonium salt obtained in step (i) with formoxime $CH_2$=N—OH in the presence of a copper salt, where step (ii) is carried out at a pH of more than 5.
This method is referred to hereinafter as method A.

The invention also relates to a method for preparing isoxazoline compounds of formula III

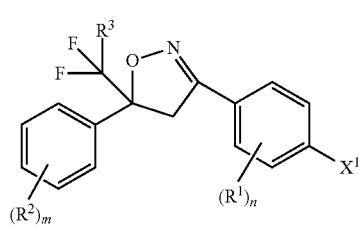

(III)

wherein
$R^1$, n and $X^1$ are as defined above;

each $R^2$ is independently selected from F, Cl, cyano, azido, nitro, —SCN, $SF_5$, $C_1$-$C_6$-alkyl, $C_1$-$C_6$-haloalkyl, $C_3$-$C_8$-cycloalkyl, $C_3$-$C_8$-halocycloalkyl, —$OR^4$, —$Si(R^5)_2R^6$, phenyl which may be substituted by 1, 2, 3, 4 or 5 radicals $R^7$, and a 3-, 4-, 5-, 6- or 7-membered saturated, partially unsaturated or completely unsaturated heterocyclic ring containing 1, 2 or 3 heteroatoms or heteroatom groups selected from N, O, S, NO, SO and $SO_2$, as ring members, where the heterocyclic ring may be substituted by one or more radicals $R^7$;

$R^3$ is selected from H, F, Cl or $CF_3$;

$R^4$ is selected from the group consisting of $C_1$-$C_6$-alkyl, $C_1$-$C_8$-haloalkyl, $C_3$-$C_8$-cycloalkyl, $C_3$-$C_8$-cycloalkyl-$C_1$-$C_4$-alkyl, phenyl which may be substituted by 1, 2, 3, 4 or 5 radicals $R^7$, and a 3-, 4-, 5-, 6- or 7-membered saturated, partially unsaturated or completely unsaturated heterocyclic ring containing 1, 2 or 3 heteroatoms or heteroatom groups selected from N, O, S, NO, SO and $SO_2$, as ring members, where the heterocyclic ring may be substituted by one or more radicals $R^7$;

$R^5$, $R^6$ are, independently of each other and independently of each occurrence, selected from the group consisting of $C_1$-$C_4$-alkyl, $C_3$-$C_8$-cycloalkyl, $C_1$-$C_4$-alkoxy-$C_1$-$C_4$-alkyl, phenyl and benzyl;

each $R^7$ is independently selected from the group consisting of F, Cl, cyano, azido, nitro, —SCN, $SF_5$ and $C_1$-$C_{10}$-alkyl which may be partially or fully halogenated; and m is 0, 1, 2 or 3;

which method comprises following steps:

(i) reacting an aniline compound of formula II

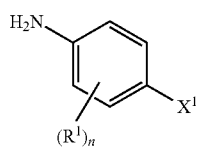

(II)

wherein $R^1$, n and $X^1$ are as defined above,
with a nitrite salt in an acidic medium to a diazonium salt; and (ii) reacting the diazonium salt obtained in step (i) with formoxime $CH_2$=N—OH in the presence of a copper salt, where step (ii) is carried out at a pH of more than 5.

This method is referred to hereinafter as method B.

The invention further relates to a method for preparing isoxazoline compounds of formula IV

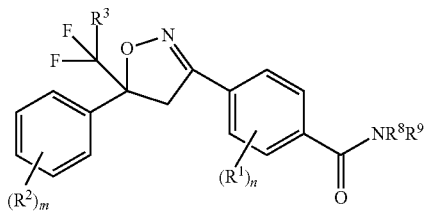

(IV)

wherein
$R^1$, $R^2$, $R^3$, $X^1$, n and m are as defined above;
$R^8$ is selected from H, $C_1$-$C_6$-alkyl which may carry 1, 2, 3 or 4 substituents $R^{10}$, and Z-A,
wherein
Z is a chemical bond, $CH_2$, $CH_2CH_2$ or C=O;

A is selected from the group consisting of

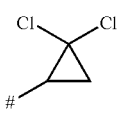 A-1

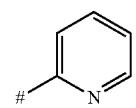 A-2

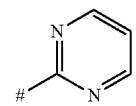 A-3

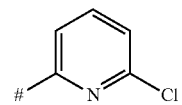 A-4

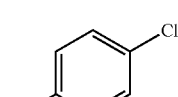 A-5

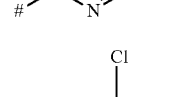 A-6

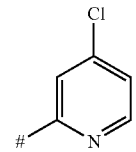 A-7

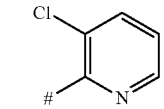 A-8

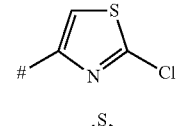 A-9

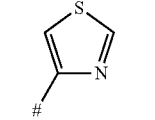 A-10

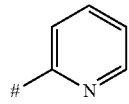 A-11

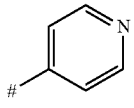 A-12

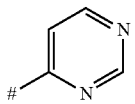 A-13

A-14 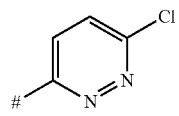

A-15 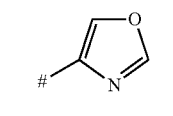

A-16 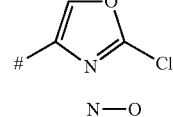

A-17 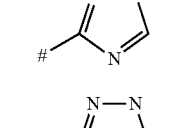

A-18 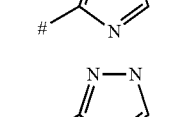

A-19 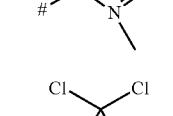

A-20 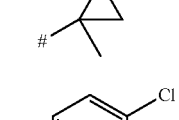

A-21 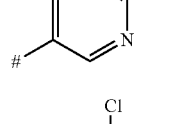

A-22 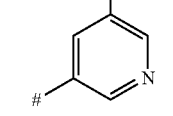

A-23 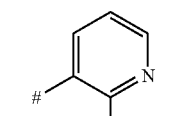

A-24 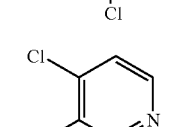

A-25 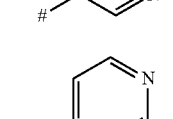

A-26 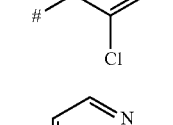

A-27 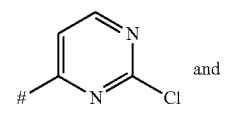
and

A-28 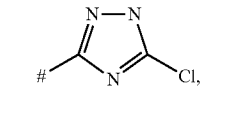

and wherein the "#" in the formulae of variables A indicate the attachment point to Z;

each $R^{10}$ is independently selected from the group consisting of halogen, cyano, azido, nitro, —SCN, $SF_5$, $C_1$-$C_6$-alkyl, $C_1$-$C_6$-haloalkyl, $C_1$-$C_6$-alkoxy-$C_1$-$C_6$-alkyl, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, —Si$(R^{17})_2R^{18}$, —$OR^{11}$, —$OSO_2R^{11}$, —$SR^{11}$, —$S(O)_mR^{11}$, —$S(O)_nN(R^{12})R^{13}$, —$N(R^{12})R^{13}$, —$C(=O)N(R^{12})R^{13}$, —$C(=S)N(R^{12})R^{13}$, —$C(=O)OR^{11}$, phenyl which may be substituted by 1, 2, 3, 4 or 5 radicals $R^{14}$, and a 3-, 4-, 5-, 6- or 7-membered saturated, partially unsaturated or completely unsaturated heterocyclic ring containing 1, 2 or 3 heteroatoms or heteroatom groups selected from N, O, S, NO, SO and $SO_2$, as ring members, where the heterocyclic ring may be substituted by one or more radicals $R^{14}$;

or two geminally bound radicals $R^{10}$ together form a group selected from =$CR^{15}R^{16}$, =$S(O)_mR^{11}$, =$S(O)_mN(R^{12})R^{13}$, =$NR^{12}$, =$NOR^{11}$ and =$NNR^{12}$;

or two radicals $R^{10}$, together with the carbon atoms to which they are bound, form a 3-, 4-, 5-, 6-, 7- or 8-membered saturated or partially unsaturated carbocyclic or heterocyclic ring containing 1, 2 or 3 heteroatoms or heteroatom groups selected from N, O, S, NO, SO and $SO_2$, as ring members;

wherein $R^{11}$ is selected from the group consisting of hydrogen, cyano, $C_1$-$C_6$-alkyl, $C_2$-$C_6$-alkenyl, $C_2$-$C_6$-alkynyl, $C_3$-$C_8$-cycloalkyl, wherein the four last mentioned radicals may be unsubstituted, partially or fully halogenated and/or wherein one or two $CH_2$ groups may be replaced by a CO group; and/or may carry 1 or 2 radicals selected from $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_1$-$C_6$-alkoxycarbonyl, trimethylsilyl, triethylsilyl, tert-butyldimethylsilyl, phenyl, benzyl, pyridyl and phenoxy, it being possible for phenyl, benzyl, pyridyl and phenoxy to be unsubstituted, partially or fully halogenated and/or to carry 1, 2 or 3 substituents selected from the group consisting of $C_1$-$C_6$-alkyl, $C_1$-$C_6$-haloalkyl, $C_1$-$C_6$-alkoxy, $C_1$-$C_6$ haloalkoxy and $C_1$-$C_6$-alkoxycarbonyl;

$R^{12}$, $R^{13}$ are, independently from one another, selected from the group consisting of hydrogen, cyano, $C_1$-$C_6$-alkyl, $C_2$-$C_6$-alkenyl, $C_2$-$C_6$-alkynyl, $C_3$-$C_8$-cycloalkyl, wherein the four last mentioned radicals may be unsubstituted, partially or fully halogenated and/or wherein one or two $CH_2$ groups may be replaced by a CO group; and/or may carry 1 or 2 radicals selected from $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_1$-$C_6$-alkoxycarbonyl, trimethylsilyl, triethylsilyl, tert-butyldimethylsilyl, phenyl, benzyl, pyridyl and phenoxy, it being possible for phenyl, benzyl, pyridyl and phenoxy to be unsubstituted, partially or fully halogenated and/or to carry 1, 2 or 3 substituents selected from the group consisting of $C_1$-$C_6$-alkyl, $C_1$-$C_6$-haloalkyl, $C_1$-$C_6$-alkoxy, $C_1$-$C_6$ haloalkoxy and $C_1$-$C_6$-alkoxycarbonyl;

or, $R^{12}$ and $R^{13}$, together with the nitrogen atom to which they are bound, form a 3-, 4-, 5-, 6- or 7-membered saturated, partly unsaturated or completely unsaturated heterocyclic ring which may contain 1 or 2 further heteroatoms selected from N, O and S as ring members, where the heterocyclic ring may carry 1, 2, 3 or 4 substituents selected from halogen, $C_1$-$C_4$-alkyl, $C_1$-$C_4$-haloalkyl, $C_1$-$C_4$-alkoxy and $C_1$-$C_4$-haloalkoxy;

each $R^{14}$ is, independently of each occurrence and independently from one another, selected from the group consisting of hydrogen, cyano, $C_1$-$C_6$-alkyl, $C_2$-$C_6$-alkenyl, $C_2$-$C_6$-alkynyl and $C_3$-$C_8$-cycloalkyl, where the four last-mentioned radicals may be unsubstituted, partially or fully halogenated and/or wherein one or two $CH_2$ groups may be replaced by a CO group, and/or may carry 1 or 2 radicals selected from $C_1$-$C_4$-alkoxy, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_1$-$C_6$-alkoxycarbonyl trimethylsilyl, triethylsilyl, tert-butyldimethylsilyl, phenyl, benzyl, pyridyl and phenoxy, it being possible for phenyl, benzyl, pyridyl and phenoxy to be unsubstituted, partially or fully halogenated and/or to carry 1, 2 or 3 substituents selected from the group consisting of $C_1$-$C_6$-alkyl, $C_1$-$C_6$-haloalkyl, $C_1$-$C_6$-alkoxy, $C_1$-$C_6$ haloalkoxy and $C_1$-$C_6$-alkoxycarbonyl;

or two radicals $R^{14}$ together form a group $=C(C_1$-$C_4$-alky)$_2$, $=N(C_1$-$C_6$-alky), $=NO(C_1$-$C_6$-alky); or $=O$;

or, two radicals $R^{14}$ bound to the same nitrogen atom, together with this nitrogen atom form a 3-, 4-, 5-, 6- or 7-membered saturated, partly unsaturated or completely unsaturated ring which may contain 1 or 2 further heteroatoms selected from N, O and S as ring members, where the heterocyclic ring may carry 1 or 2 substituents selected from halogen, $C_1$-$C_4$-haloalkyl, $C_1$-$C_4$-alkoxy and $C_1$-$C_4$-haloalkoxy;

$R^{15}$, $R^{16}$ are, independently from one another, selected from the group consisting of hydrogen, halogen, cyano, azido, nitro, —SCN, $SF_5$, $C_1$-$C_6$-alkyl, $C_2$-$C_6$-alkenyl, $C_2$-$C_6$-alkynyl and $C_3$-$C_8$-cycloalkyl, where the four last mentioned radicals may be unsubstituted, partially or fully halogenated and/or oxygenated, and/or may carry 1 or 2 radicals selected from $C_1$-$C_4$-alkyl; $C_1$-$C_4$-haloalkyl; $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, —OH, —SH, phenyl, benzyl, pyridyl and phenoxy, it being possible for phenyl, benzyl, pyridyl and phenoxy to be unsubstituted, partially or fully halogenated and/or to carry 1, 2 or 3 substituents selected from the group consisting of $C_1$-$C_6$-alkyl, $C_1$-$C_6$-haloalkyl, $C_1$-$C_6$-alkoxy, $C_1$-$C_6$ haloalkoxy; ($C_1$-$C_6$-alkoxy)carbonyl, ($C_1$-$C_6$-alkyl)amino, di-($C_1$-$C_6$-alkyl)amino;

or $R^{15}$ and $R^{16}$ together form a group $=C(C_1$-$C_4$-alky)$_2$, $=N(C_1$-$C_6$-alky), $=NO(C_1$-$C_6$-alky), or $=O$;

$R^{17}$, $R^{18}$ are, independently of each other, selected from the group consisting of $C_1$-$C_4$-alkyl, $C_3$-$C_6$-cycloalkyl, $C_1$-$C_4$-alkoxy-$C_1$-$C_4$-alkyl, phenyl and benzyl;

and $R^9$ is selected from H, $CH_3$, $CH_2CH_3$, $CH_2CH_2CH_3$, $C(=O)CH_3$ and $C(=O)OCH_3$;

which method comprises following steps:

(i) reacting an aniline compound of formula II

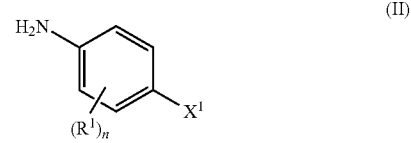

wherein $R^1$, n and $X^1$ are as defined above, with a nitrite salt in an acidic medium to a diazonium salt; and (ii) reacting the diazonium salt obtained in step (i) with formoxime $CH_2=N-OH$ in the presence of a copper salt, where step (ii) is carried out at a pH of more than 5.

This method is referred to hereinafter as method C.

The organic moieties mentioned in the above definitions of the variables are—like the term halogen—collective terms for individual listings of the individual group members. The prefix $C_n$-$C_m$ indicates in each case the possible number of carbon atoms in the group.

The term halogen, if not specified otherwise, denotes in each case fluorine, bromine, chlorine or iodine, in particular fluorine, chlorine or bromine.

The term "$C_1$-$C_{10}$-alkyl" as used herein and in the alkyl moieties of alkoxy, alkylthio, alkylsulfinyl, alkylsulfonyl, alkylcarbonyl, alkoxycarbonyl and the like refers to saturated straight-chain or branched hydrocarbon radicals having 1 to 2 ("$C_1$-$C_2$-alkyl"), 1 to 4 ("$C_1$-$C_4$-alkyl"), 1 to 6 ("$C_1$-$C_6$-alkyl"), 1 to 8 ("$C_1$-$C_8$-alkyl") or 1 to 10 ("$C_1$-$C_{10}$-alkyl") carbon atoms. $C_1$-$C_2$-Alkyl is methyl or ethyl. $C_1$-$C_4$-Alkyl is additionally propyl, isopropyl, butyl, 1-methylpropyl (sec-butyl), 2-methylpropyl (isobutyl) or 1,1-dimethylethyl (tert-butyl). $C_1$-$C_6$-Alkyl is additionally also, for example, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methylpropyl. $C_1$-$C_8$-Alkyl is additionally also, for example, heptyl, octyl, 2-ethylhexyl and positional isomers thereof. $C_1$-$C_{10}$-Alkyl is additionally also, for example, nonyl, decyl and positional isomers thereof.

The term "$C_1$-$C_{10}$-haloalkyl" as used herein, which is also expressed as "$C_1$-$C_{10}$-alkyl which is partially or fully halogenated", refers to straight-chain or branched alkyl groups having 1 to 2 ("$C_1$-$C_2$-haloalkyl"), 1 to 4 ("$C_1$-$C_4$-haloalkyl"), 1 to 6 ("$C_1$-$C_6$-haloalkyl"), 1 to 8 ("$C_1$-$C_8$-haloalkyl") or 1 to 10 ("$C_1$-$C_{10}$-haloalkyl") carbon atoms (as mentioned above), where some or all of the hydrogen atoms in these groups are replaced by halogen atoms selected from fluorine and chlorine: in particular $C_1$-$C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl or 1,1,1-trifluoroprop-2-yl.

"Halomethyl" is methyl in which 1, 2 or 3 of the hydrogen atoms are replaced by halogen atoms selected from fluorine and chlorine. Examples are chloromethyl, fluoromethyl, dichloromethyl, trichloromethyl, difluoromethyl, trifluoromethyl, chlorofluoromethyl, dichlorofluoromethyl, chlorodifluoromethyl and the like.

The term "$C_2$-$C_{10}$-alkenyl" as used herein and in the alkenyl moiety of alkenyloxy and the like refers to monounsaturated straight-chain or branched hydrocarbon radicals having 2 to 4 ("$C_2$-$C_4$-alkenyl"), 2 to 6 ("$C_2$-$C_6$-alkenyl"), 2 to 8 ("$C_2$-$C_8$-alkenyl"), 3 to 8 ("$C_3$-$C_8$-alkenyl"), 2 to 10 ("$C_2$-$C_{10}$-alkenyl") or 3 to 10 ("$C_3$-$C_{10}$-alkenyl") carbon atoms and a double bond in any position, for example $C_2$-$C_4$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl or 2-methyl-2-propenyl; $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl and the like, or $C_2$-$C_{10}$-alkenyl, such as the radicals mentioned for $C_2$-$C_6$-alkenyl and additionally 1-heptenyl, 2-heptenyl, 3-heptenyl, 1-octenyl, 2-octenyl, 3-octenyl, 4-octenyl, 1-nonenyl, 2-nonenyl, 3-nonenyl, 4-nonenyl, 1-decenyl, 2-decenyl, 3-decenyl, 4-decenyl, 5-decenyl and the positional isomers thereof.

The term "$C_2$-$C_{10}$-haloalkenyl" as used herein, which is also expressed as "$C_1$-$C_{10}$-alkenyl which is partially or fully halogenated", and the haloalkenyl moieties in haloalkenyloxy, haloalkenylcarbonyl and the like refers to unsaturated straight-chain or branched hydrocarbon radicals having 2 to 4 ("$C_2$-$C_4$-haloalkenyl"), 2 to 6 ("$C_2$-$C_6$-haloalkenyl"), 2 to 8 ("$C_2$-$C_8$-haloalkenyl") or 2 to 10 ("$C_2$-$C_{10}$-haloalkenyl") carbon atoms and a double bond in any position (as mentioned above), where some or all of the hydrogen atoms in these groups are replaced by halogen atoms selected from fluorine and chlorine, for example chlorovinyl, chloroallyl and the like.

The term "$C_2$-$C_{10}$-alkynyl" as used herein and the alkynyl moieties in alkynyloxy, alkynylcarbonyl and the like refers to straight-chain or branched hydrocarbon groups having 2 to 4 ("$C_2$-$C_4$-alkynyl"), 2 to 6 ("$C_2$-$C_6$-alkynyl"), 2 to 8 ("$C_2$-$C_8$-alkynyl"), 3 to 8 ("$C_3$-$C_8$-alkynyl"), 2 to 10 ("$C_2$-$C_{10}$-alkynyl") or 3 to 10 ("$C_3$-$C_8$-alkynyl") carbon atoms and one or two triple bonds in any position, for example $C_2$-$C_4$-alkynyl, such as ethynyl, 1-propynyl, 2-propynyl, 1-butynyl, 2-butynyl, 3-butynyl, 1-methyl-2-propynyl and the like, $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl and the like;

The term "$C_2$-$C_{10}$-haloalkynyl" as used herein, which is also expressed as "$C_1$-$C_{10}$-alkynyl which is partially or fully halogenated", and the haloalkynyl moieties in haloalkynyloxy, haloalkynylcarbonyl and the like refers to unsaturated straight-chain or branched hydrocarbon radicals having 2 to 4 ("$C_2$-$C_4$-haloalkynyl"), 3 to 4 ("$C_3$-$C_4$-haloalkynyl"), 2 to 6 ("$C_2$-$C_6$-haloalkynyl"), 3 to 6 ("$C_3$-$C_6$-haloalkynyl"), 2 to 8 ("$C_2$-$C_8$-haloalkynyl"), 3 to 8 ("$C_3$-$C_8$-haloalkynyl"), 2 to 10 ("$C_2$-$C_{10}$-haloalkynyl") or 3 to 10 ("$C_3$-$C_{10}$-haloalkynyl") carbon atoms and one or two triple bonds in any position (as mentioned above), where some or all of the hydrogen atoms in these groups are replaced by halogen atoms selected from fluorine and chlorine;

The term "$C_3$-$C_8$-cycloalkyl" as used herein refers to mono- or bi- or polycyclic saturated hydrocarbon radicals having 3 to 8, in particular 3 to 6 carbon atoms ("$C_3$-$C_6$-cycloalkyl"). Examples of monocyclic radicals having 3 to 6 carbon atoms comprise cyclopropyl, cyclobutyl, cyclopentyl and cyclohexyl. Examples of monocyclic radicals having 3 to 8 carbon atoms comprise cyclopropyl, cyclobutyl, cyclopentyl, cyclohexyl, cycloheptyl and cyclooctyl. Examples of bicyclic radicals having 7 or 8 carbon atoms comprise bicyclo[2.2.1]heptyl, bicyclo[3.1.1]heptyl, bicyclo[2.2.2]octyl and bicyclo[3.2.1]octyl.

The term "$C_3$-$C_8$-halocycloalkyl" as used herein, which is also expressed as "$C_3$-$C_8$-cycloalkyl which is partially or fully halogenated", and the halocycloalkyl moieties in halocycloalkoxy, halocycloalkylcarbonyl and the like refers to mono- or bi- or polycyclic saturated hydrocarbon groups having 3 to 8 ("$C_3$-$C_8$-halocycloalkyl") or preferably 3 to 6 ("$C_3$-$C_6$-halocycloalkyl") carbon ring members (as mentioned above) in which some or all of the hydrogen atoms are replaced by halogen atoms selected from fluorine and chlorine.

The term "$C_3$-$C_8$-cycloalkyl-$C_1$-$C_4$-alkyl" refers to a $C_3$-$C_8$-cycloalkyl group as defined above which is bound to the remainder of the molecule via a $C_1$-$C_4$-alkyl group, as defined above. Examples are cyclopropylmethyl, cyclopropylethyl, cyclopropylpropyl, cyclobutylmethyl, cyclobutylethyl, cyclobutylpropyl, cyclopentylmethyl, cyclopentylethyl, cyclopentylpropyl, cyclohexylmethyl, cyclohexylethyl, cyclohexylpropyl, and the like.

The term "$C_3$-$C_8$-halocycloalkyl-$C_1$-$C_4$-alkyl" refers to a $C_3$-$C_8$-halocycloalkyl group as defined above which is bound to the remainder of the molecule via a $C_1$-$C_4$-alkyl group, as defined above.

The term "$C_1$-$C_2$-alkoxy" is a $C_1$-$C_2$-alkyl group, as defined above, attached via an oxygen atom. The term "$C_1$-$C_4$-alkoxy" is a $C_1$-$C_4$-alkyl group, as defined above, attached via an oxygen atom. The term "$C_1$-$C_6$-alkoxy" is a $C_1$-$C_6$-alkyl group, as defined above, attached via an oxygen atom. The term "$C_1$-$C_{10}$-alkoxy" is a $C_1$-$C_{10}$-alkyl group, as defined above, attached via an oxygen atom. $C_1$-$C_2$-Alkoxy is methoxy or ethoxy. $C_1$-$C_4$-Alkoxy is additionally, for example, n-propoxy, 1-methylethoxy (isopropoxy), butoxy, 1-methylpropoxy (sec-butoxy), 2-methylpropoxy (isobutoxy) or 1,1-dimethylethoxy (tert-butoxy). $C_1$-$C_6$-Alkoxy is additionally, for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy. $C_1$-$C_8$-Alkoxy is additionally, for example, heptyloxy, octyloxy, 2-ethylhexyloxy and positional isomers thereof. $C_1$-$C_{10}$-Alkoxy is additionally, for example, nonyloxy, decyloxy and positional isomers thereof.

The term "$C_1$-$C_2$-haloalkoxy" is a $C_1$-$C_2$-haloalkyl group, as defined above, attached via an oxygen atom. The term "$C_1$-$C_4$-haloalkoxy" is a $C_1$-$C_4$-haloalkyl group, as defined above, attached via an oxygen atom. The term "$C_1$-$C_6$-haloalkoxy" is a $C_1$-$C_6$-haloalkyl group, as defined above, attached via an oxygen atom. The term "$C_1$-$C_{10}$-haloalkoxy" is a $C_1$-$C_{10}$-haloalkyl group, as defined above, attached via an oxygen atom. $C_1$-$C_2$-Haloalkoxy is, for example, $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or $OC_2F_5$. $C_1$-$C_4$-Haloalkoxy is additionally, for example, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy, 4-fluorobutoxy, 4-chlorobutoxy, or nonafluorobutoxy. $C_1$-$C_6$-Haloalkoxy is additionally, for example, 5-fluoropentoxy, 5-chloropentoxy, undecafluoropentoxy, 6-fluorohexoxy, 6-chlorohexoxy, or dodecafluorohexoxy.

The term "$C_1$-$C_2$-alkylthio" is a $C_1$-$C_2$-alkyl group, as defined above, attached via a sulfur atom. The term "$C_1$-$C_4$-alkylthio" is a $C_1$-$C_4$-alkyl group, as defined above, attached via a sulfur atom. The term "$C_1$-$C_6$-alkylthio" is a $C_1$-$C_6$-alkyl group, as defined above, attached via a sulfur atom. The term "$C_1$-$C_{10}$-alkylthio" is a $C_1$-$C_{10}$-alkyl group, as defined above, attached via a sulfur atom. $C_1$-$C_2$-Alkylthio is methylthio or ethylthio. $C_1$-$C_4$-Alkylthio is additionally, for example, n-propylthio, 1-methylethylthio (isopropylthio), butylthio, 1-methylpropylthio (sec-butylthio), 2-methylpropylthio (isobutylthio) or 1,1-dimethylethylthio (tert-butylthio). $C_1$-$C_6$-Alkylthio is additionally, for example, pentylthio, 1-methylbutylthio, 2-methylbutylthio, 3-methylbutylthio, 1,1-dimethylpropylthio, 1,2-dimethylpropylthio, 2,2-dimethylpropylthio, 1-ethylpropylthio, hexylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio. $C_1$-$C_8$-Alkylthio is additionally, for example, heptylthio, octylthio, 2-ethylhexylthio and positional isomers thereof. $C_1$-$C_{10}$-Alkylthio is additionally, for example, nonylthio, decylthio and positional isomers thereof.

The term "$C_1$-$C_2$-haloalkylthio" is a $C_1$-$C_2$-haloalkyl group, as defined above, attached via a sulfur atom. The term "$C_1$-$C_4$-haloalkylthio" is a $C_1$-$C_4$-haloalkyl group, as defined above, attached via a sulfur atom. The term "$C_1$-$C_6$-haloalkylthio" is a $C_1$-$C_6$-haloalkyl group, as defined above, attached via a sulfur atom. The term "$C_1$-$C_{10}$-haloalkylthio" is a $C_1$-$C_{10}$-haloalkyl group, as defined above, attached via a sulfur atom. $C_1$-$C_2$-Haloalkylthio is, for example, $SCH_2F$, $SCHF_2$, $SCF_3$, $SCH_2Cl$, $SCHCl_2$, $SCCl_3$, chlorofluoromethylthio, dichlorofluoromethylthio, chlorodifluoromethylthio, 2-fluoroethylthio, 2-chloroethylthio, 22,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or $SC_2F_5$. $C_1$-$C_4$-Haloalkylthio is additionally, for example, 2-fluoropropylthio, 3-fluoropropylthio, 2,2-difluoropropylthio, 2,3-difluoropropylthio, 2-chloropropylthio, 3-chloropropylthio, 2,3-dichloropropylthio, 3,3,3-trifluoropropylthio, 3,3,3-trichloropropylthio, $SCH_2$—$C_2F_5$, $SCF_2$—$C_2F_5$, 1-($CH_2F$)-2-fluoroethylthio, 1-($CH_2Cl$)-2-chloroethylthio, 4-fluorobutylthio, 4-chlorobutylthio, or nonafluorobutylthio. $C_1$-$C_6$-Haloalkylthio is additionally, for example, 5-fluoropentylthio, 5-chloropentylthio, undecafluoropentylthio, 6-fluorohexylthio, 6-chlorohexylthio, or dodecafluorohexylthio.

The term "$C_1$-$C_2$-alkylsulfinyl" is a $C_1$-$C_2$-alkyl group, as defined above, attached via a sulfinyl [S(O)] group. The term "$C_1$-$C_4$-alkylsulfinyl" is a $C_1$-$C_4$-alkyl group, as defined above, attached via a sulfinyl [S(O)] group. The term "$C_1$-$C_6$-alkylsulfinyl" is a $C_1$-$C_6$-alkyl group, as defined above, attached via a sulfinyl [S(O)] group. The term "$C_1$-$C_{10}$-alkylsulfinyl" is a $C_1$-$C_{10}$-alkyl group, as defined above, attached via a sulfinyl [S(O)] group. $C_1$-$C_2$-Alkylsulfinyl is methylsulfinyl or ethylsulfinyl. $C_1$-$C_4$-Alkylsulfinyl is additionally, for example, n-propylsulfinyl, 1-methylethylsulfinyl (isopropylsulfinyl), butylsulfinyl, 1-methylpropylsulfinyl (sec-butylsulfinyl), 2-methylpropylsulfinyl (isobutylsulfinyl) or 1,1-dimethylethylsulfinyl (tert-butylsulfinyl). $C_1$-$C_6$-Alkylsulfinyl is additionally, for example, pentylsulfinyl, 1-methylbutylsulfinyl, 2-methylbutylsulfinyl, 3-methylbutylsulfinyl, 1,1-dimethylpropylsulfinyl, 1,2-dimethylpropylsulfinyl, 2,2-dimethylpropylsulfinyl, 1-ethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl. $C_1$-$C_8$-Alkylsulfinyl is additionally, for example, heptylsulfinyl, octylsulfinyl, 2-ethylhexylsulfinyl and positional isomers thereof. $C_1$-$C_{10}$-Alkylsulfinyl is additionally, for example, nonylsulfinyl, decylsulfinyl and positional isomers thereof.

The term "$C_1$-$C_2$-haloalkylsulfinyl" is a $C_1$-$C_2$-haloalkyl group, as defined above, attached via a sulfinyl [S(O)] group. The term "$C_1$-$C_4$-haloalkylsulfinyl" is a $C_1$-$C_4$-haloalkyl group, as defined above, attached via a sulfinyl [S(O)] group.

The term "$C_1$-$C_6$-haloalkylsulfinyl" is a $C_1$-$C_6$-haloalkyl group, as defined above, attached via a sulfinyl [S(O)] group. The term "$C_1$-$C_{10}$-haloalkylsulfinyl" is a $C_1$-$C_{10}$-haloalkyl group, as defined above, attached via a sulfinyl [S(O)] group. $C_1$-$C_2$-Haloalkylsulfinyl is, for example, S(O)CH$_2$F, S(O)CHF$_2$, S(O)CF$_3$, S(O)CH$_2$Cl, S(O)CHCl$_2$, S(O)CCl$_3$, chlorofluoromethylsulfinyl, dichlorofluoromethylsulfinyl, chlorodifluoromethylsulfinyl, 2-fluoroethylsulfinyl, 2-chloroethylsulfinyl, 2,2-difluoroethylsulfinyl, 2,2,2-trifluoroethylsulfinyl, 2-chloro-2-fluoroethylsulfinyl, 2-chloro-2,2-difluoroethylsulfinyl, 2,2-dichloro-2-fluoroethylsulfinyl, 2,2,2-trichloroethylsulfinyl or S(O)C$_2$F$_5$. $C_1$-$C_4$-Haloalkylsulfinyl is additionally, for example, 2-fluoropropylsulfinyl, 3-fluoropropylsulfinyl, 2,2-difluoropropylsulfinyl, 2,3-difluoropropylsulfinyl, 2-chloropropylsulfinyl, 3-chloropropylsulfinyl, 2,3-dichloropropylsulfinyl, 3,3,3-trifluoropropylsulfinyl, 3,3,3-trichloropropylsulfinyl, S(O)CH$_2$—C$_2$F$_5$, S(O)CF$_2$—C$_2$F$_5$, 1-(CH$_2$F)-2-fluoroethylsulfinyl, 1-(CH$_2$Cl)-2-chloroethylsulfinyl, 4-fluorobutylsulfinyl, 4-chlorobutylsulfinyl, or nonafluorobutylsulfinyl. $C_1$-$C_6$-Haloalkylsulfinyl is additionally, for example, 5-fluoropentylsulfinyl, 5-chloropentylsulfinyl, undecafluoropentylsulfinyl, 6-fluorohexylsulfinyl, 6-chlorohexylsulfinyl, or dodecafluorohexylsulfinyl.

The term "$C_1$-$C_2$-alkylsulfonyl" is a $C_1$-$C_2$-alkyl group, as defined above, attached via a sulfonyl [S(O)$_2$] group. The term "$C_1$-$C_4$-alkylsulfonyl" is a $C_1$-$C_4$-alkyl group, as defined above, attached via a sulfonyl [S(O)$_2$] group. The term "$C_1$-$C_6$-alkylsulfonyl" is a $C_1$-$C_6$-alkyl group, as defined above, attached via a sulfonyl [S(O)$_2$] group. The term "$C_1$-$C_{10}$-alkylsulfonyl" is a $C_1$-$C_{10}$-alkyl group, as defined above, attached via a sulfonyl [S(O)$_2$] group. $C_1$-$C_2$-Alkylsulfonyl is methylsulfonyl or ethylsulfonyl. $C_1$-$C_4$-Alkylsulfonyl is additionally, for example, n-propylsulfonyl, 1-methylethylsulfonyl (isopropylsulfonyl), butylsulfonyl, 1-methylpropylsulfonyl (sec-butylsulfonyl), 2-methylpropylsulfonyl (isobutylsulfonyl) or 1,1-dimethylethylsulfonyl (tert-butylsulfonyl). $C_1$-$C_6$-Alkylsulfonyl is additionally, for example, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl. $C_1$-$C_8$-Alkylsulfonyl is additionally, for example, heptylsulfonyl, octylsulfonyl, 2-ethylhexylsulfonyl and positional isomers thereof. $C_1$-$C_{10}$-Alkylsulfonyl is additionally, for example, nonylsulfonyl, decylsulfonyl and positional isomers thereof.

The term "$C_1$-$C_2$-haloalkylsulfonyl" is a $C_1$-$C_2$-haloalkyl group, as defined above, attached via a sulfonyl [S(O)$_2$] group. The term "$C_1$-$C_4$-haloalkylsulfonyl" is a $C_1$-$C_4$-haloalkyl group, as defined above, attached via a sulfonyl [S(O)$_2$] group. The term "$C_1$-$C_6$-haloalkylsulfonyl" is a $C_1$-$C_6$-haloalkyl group, as defined above, attached via a sulfonyl [S(O)$_2$] group. The term "$C_1$-$C_{10}$-haloalkylsulfonyl" is a $C_1$-$C_{10}$-haloalkyl group, as defined above, attached via a sulfonyl [S(O)$_2$] group. $C_1$-$C_2$-Haloalkylsulfonyl is, for example, S(O)$_2$CH$_2$F, S(O)$_2$CHF$_2$, S(O)$_2$CF$_3$, S(O)$_2$CH$_2$Cl, S(O)$_2$CHCl$_2$, S(O)$_2$CCl$_3$, chlorofluoromethylsulfonyl, dichlorofluoromethylsulfonyl, chlorodifluoromethylsulfonyl, 2-fluoroethylsulfonyl, 2-chloroethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl or S(O)$_2$C$_2$F$_5$. $C_1$-$C_4$-Haloalkylsulfonyl is additionally, for example, 2-fluoropropylsulfonyl, 3-fluoropropylsulfonyl, 2,2-difluoropropylsulfonyl, 2,3-difluoropropylsulfonyl, 2-chloropropylsulfonyl, 3-chloropropylsulfonyl, 2,3-dichloropropylsulfonyl, 3,3,3-trifluoropropylsulfonyl, 3,3,3-trichloropropylsulfonyl, S(O)$_2$CH$_2$—C$_2$F$_5$, S(O)$_2$CF$_2$—C$_2$F$_5$, 1-(CH$_2$F)-2-fluoroethylsulfonyl, 1-(CH$_2$Cl)-2-chloroethylsulfonyl, 4-fluorobutylsulfonyl, 4-chlorobutylsulfonyl, or nonafluorobutylsulfonyl. $C_1$-$C_6$-Haloalkylsulfonyl is additionally, for example, 5-fluoropentylsulfonyl, 5-chloropentylsulfonyl, undecafluoropentylsulfonyl, 6-fluorohexylsulfonyl, 6-chlorohexylsulfonyl, or dodecafluorohexylsulfonyl.

The term "3-, 4-, 5-, 6- or 7-membered saturated, partially unsaturated or completely unsaturated heterocyclic ring containing 1, 2 or 3 heteroatoms or heteroatom groups selected from N, O, S, NO, SO and SO$_2$, as ring members" as used herein refers to monocyclic radicals, the monocyclic radicals being saturated, partially unsaturated or completely unsaturated (specifically aromatic). The heterocyclic radical may be attached to the remainder of the molecule via a carbon ring member or via a nitrogen ring member.

Examples of 3-, 4-, 5-, 6- or 7-membered saturated heterocyclyl include: Oxiranyl, aziridinyl, oxetidinyl (radical of trimethylene oxide), thietidinyl (radical of trimethylene sulfide), azetidinyl, 2-tetrahydrofuranyl, 3-tetrahydrofuranyl, 1,3-dioxolane-2-yl, 1,3-dioxolane-4-yl, 2-tetrahydrothienyl, 3-tetrahydrothienyl, 1,3-thiolane-2-yl, 1,3-dithiolane-4-yl, 1-thia-3-oxolan-2-yl, 1-thia-3-oxolan-4-yl, 1-thia-3-oxolan-5-yl, 2-pyrrolidinyl, 3-pyrrolidinyl, 3-pyrazolidinyl, 4-pyrazolidinyl, 5-pyrazolidinyl, 2-imidazolidinyl, 4-imidazolidinyl, 2-oxazolidinyl, 4-oxazolidinyl, 5-oxazolidinyl, 3-isoxazolidinyl, 4-isoxazolidinyl, 5-isoxazolidinyl, 2-thiazolidinyl, 4-thiazolidinyl, 5-thiazolidinyl, 3-isothiazolidinyl, 4-isothiazolidinyl, 5-isothiazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2-tetrahydropyranyl, 3-tetrahydropyranyl, 4-tetrahydropyranyl, 1,3-dioxan-2-yl, 1,3-dioxan-4-yl, 1,3-dioxan-5-yl, 1,4-dioxan-2-yl, 2-thianyl, 3-thianyl, 4-thianyl, 1,3-dithian-2-yl, 1,3-dithian-4-yl, 1,3-dithian-5-yl, 1,4-dithian-2-yl, 1-oxa-3-thian-2-yl, 1-oxa-3-thian-4-yl, 1-oxa-3-thian-5-yl, 1-oxa-3-thian-6-yl, 1-oxa-4-thian-2-yl, 1-oxa-4-thian-3-yl, 2-piperidinyl, 3-piperidinyl, 4-piperidinyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl, 2-morpholinyl, 3-morpholinyl, 2-thiomorpholinyl, 3-thiomorpholinyl, 1-oxothiomorpholin-2-yl, 1-oxothiomorpholin-3-yl, 1,1-dioxothiomorpholin-2-yl, 1,1-dioxothiomorpholin-3-yl, hexahydroazepin-1-, -2-, -3- or -4-yl, hexahydrooxepinyl, hexahydro-1,3-diazepinyl, hexahydro-1,4-diazepinyl, hexahydro-1,3-oxazepinyl, hexahydro-1,4-oxazepinyl, hexahydro-1,3-dioxepinyl, hexahydro-1,4-dioxepinyl and the like.

Examples of 3-, 4-, 5-, 6- or 7-membered partially unsaturated heterocyclyl include: 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin- 5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-, 3-, 4-, 5- or 6-di- or tetrahydropyridinyl, 3-di- or tetrahydropyridazinyl, 4-di- or tetrahydropyridazinyl, 2-di- or tetrahydropyrimidinyl, 4-di- or tetrahydropyrimidinyl, 5-di- or tetrahydropyrimidinyl, di- or tetrahydropyrazinyl, 1,3,5-di- or tetrahydrotriazin-2-yl, 1,2,4-di- or tetrahydrotriazin-3-yl, 2,3,4,5-tetrahydro[1H]azepin-1-, -2-, -3-, -4-, -5-, -6- or -7-yl, 3,4,5,6-tetrahydro[2H]azepin-2-, -3-, -4-, -5-, -6- or -7-yl, 2,3,4,7-tetrahydro[1H]azepin-1-, -2-, -3-, -4-, -5-, -6- or -7-yl, 2,3,6,7-tetrahydro[1H]azepin-1-, -2-, -3-, -4-, -5-, -6- or -7-yl, tetrahydrooxepinyl, such as 2,3,4,5-tetrahydro[1H]oxepin-2-, -3-, -4-, -5-, -6- or -7-yl, 2,3,4,7-tetrahydro[1H]oxepin-2-, -3-, -4-, -5-, -6- or -7-yl, 2,3,6,7-tetrahydro[1H]oxepin-2-, -3-, -4-, -5-, -6- or -7-yl, tetrahydro-1,3-diazepinyl, tetrahydro-1,4-diazepinyl, tetrahydro-1,3-oxazepinyl, tetrahydro-1,4-oxazepinyl, tetrahydro-1,3-dioxepinyl and tetrahydro-1,4-dioxepinyl.

3-, 4-, 5-, 6- or 7-membered aromatic heterocyclyl is 5- or 6-membered aromatic heterocyclyl (hetaryl). Examples are: 2-furyl, 3-furyl, 2-thienyl, 3-thienyl, 2-pyrrolyl, 3-pyrrolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl and 2-pyrazinyl.

Aryl is phenyl, tolyl or naphthyl, specifically phenyl.

$C_1$-$C_4$-alkylene is divalent branched or preferably unbranched saturated aliphatic chain having 1 to 4 carbon atoms, for example $CH_2$, $CH_2CH_2$, —$CH(CH_3)$—, $CH_2CH_2CH_2$, $CH(CH_3)CH_2$, $CH_2CH(CH_3)$, $CH_2CH_2CH_2CH_2$.

$C_2$-$C_7$-alkylene is divalent branched or preferably unbranched saturated aliphatic chain having 2 to 7 carbon atoms, for example $CH_2CH_2$, —$CH(CH_3)$—, $CH_2CH_2CH_2$, $CH(CH_3)CH_2$, $CH_2CH(CH_3)$, $CH_2CH_2CH_2CH_2$, $CH_2CH_2CH_2CH_2CH_2$, $CH_2CH_2CH_2CH_2CH_2CH_2$, and $CH_2CH_2CH_2CH_2CH_2CH_2CH_2$ The remarks made below regarding preferred embodiments of the methods according to the invention, especially regarding preferred embodiments of the radicals of the different reactants and products and of the reaction conditions of the methods according to the invention, apply either taken alone or, more particularly, in any conceivable combination with one another. The remarks regarding preferred embodiments apply to methods A, B and C of the invention, as far as they overlap and if not specified otherwise.

The reactions described herein are carried out in reaction vessels customary for such reactions, the reaction being configurable continuously, semicontinuously or batchwise.

It has been found that carrying out step (ii) at a pH above 5 has several advantages over a method wherein step (ii) is performed at a lower pH, i.e. of at most 5, e.g. 4 or 3. For instance, the product obtained at a pH of >5 is crystalline and can be easily isolated from the reaction mixture, while a lower pH leads to a tar-like product the isolation and purification of which is very intricate. On the other side, the isolation and purification of the oxime product is indispensable as otherwise the subsequent reactions don't work or only with poor yields.

Preferably, step (ii) is carried out at a pH of at least 5.1, e.g. 5.1 to 14, preferably 5.1 to 10, e.g. 5.1 to 8 or 5.1 to 7; more preferably at a pH of at least 5.2, e.g. 5.2 to 14, preferably 5.2 to 10, e.g. 5.2 to 8 or 5.2 to 7; even more preferably at a pH of at least 5.3, e.g. 5.3 to 14, preferably 5.3 to 10, e.g. 5.3 to 8 or 5.3 to 7; and in particular at a pH of at least 5.5, e.g. 5.5 to 14, preferably 5.5 to 10, e.g. 5.5 to 8 or 5.5 to 7.

For this purpose, formoxime is preferably used in form of a solution, and this solution is preferably adjusted to a pH of >5, preferably to a pH of at least 5.1, e.g. 5.1 to 14, preferably 5.1 to 10, e.g. 5.1 to 8 or 5.1 to 7; more preferably to a pH of at least 5.2, e.g. 5.2 to 14, preferably 5.2 to 10, e.g. 5.2 to 8 or 5.2 to 7; even more preferably to a pH of at least 5.3, e.g. 5.3 to 14, preferably 5.3 to 10, e.g. 5.3 to 8 or 5.3 to 7; and in particular to a pH of at least 5.5, e.g. 5.5 to 14, preferably 5.5 to 10, e.g. 5.5 to 8 or 5.5 to 7, before it is reacted with the diazonium salt in step (ii).

As said, formoxime is preferably used in form of a solution. Suitable solvents are polar protic solvents, such as water, aqueous acidic solutions, $C_1$-$C_3$-alcohols such as methanol, ethanol, propanol and isopropanol, glycols, such as ethylene glycol and diethylene glycol, and mixtures thereof. Preferably water or aqueous acidic solutions are used.

The diazonium salt is preferably also used in the form of a solution. The solution is preferably the reaction mixture obtained in step (i), which is preferably used without further work-up or isolation or purification of the reaction product (thus for typical and preferred solvents see below description of step (i)). The pH of this solution is not critical and thus this solution may or may not be adjusted to a pH of >5 before it is reacted with formoxime in step (ii). For practical reasons it is often not adjusted to a pH>5 before reaction with formoxime, but may be introduced into the reaction of step (ii) as it is obtained in step (i), i.e. having generally a pH of ≤5.

In a preferred embodiment, the pH is controlled continuously or periodically during step (ii) to be >5, e.g. by an integrated pH meter or by periodically taking samples and determining the pH, and is adjusted if necessary to the desired pH.

The adjustment of the pH of the formoxime (solution) or of the reaction mixture of step (ii) or—optionally—of the diazonium salt (solution), is carried out depending on the starting pH. If the starting pH of the of the formoxime (solution) or of the reaction mixture of step (ii) or of the diazonium salt (solution) is for example acidic, as it is generally the case, a suitable base is added until the desired pH is achieved. If the starting pH is basic, a suitable acid is added until the desired pH is achieved. If the pH becomes acidic (i.e. 5) in the course of the reaction of step (ii) a suitable base is added until the desired pH is achieved and if inversely the pH becomes more basic in the course of the reaction of step (ii) than desired, a suitable acid is added until the desired pH is achieved.

Suitable bases are all bases which are soluble in the reaction medium. As this is preferably polar protic, bases are preferred which are soluble in polar protic solvents. Examples include hydroxides, such as lithium, sodium or potassium hydroxide, carbonates, such as lithium, sodium or potassium carbonates, hydrogen carbonates, such as lithium, sodium or potassium hydrogen carbonates, phosphates, such as lithium, sodium or potassium phosphate, hydrogen phosphate, such as lithium, sodium or potassium hydrogen phosphate, alkoxides, such as sodium or potassium methoxide, sodium or potassium ethoxide or sodium or potassium tert-butanolate, carboxylates, such as lithium, sodium or potassium formiate, lithium, sodium or potassium acetate or lithium, sodium or potassium propionate, ammonia and amines, such as dimethylamine, trimethylamine, diethylamine or triethylamine. Among these bases preference is given to using a weaker base or a combination of different bases comprising at least one weaker base which can form a buffering system and stabilize the desired pH, such as the above carbonates, the above hydrogen carbonates, the above phosphates, the above hydrogen phosphate, and the above carboxylates. Specifically, sodium acetate is used. However if the starting pH is very acidic, it is preferred to bring the pH to near 5 using a stronger base, such as the above hydroxides or alkoxides, especially sodium hydroxide or potassium hydroxide, and make the fine tuning of the pH with one of the above-listed weaker bases, especially sodium acetate, or to use a mixture of stronger and weaker bases, e.g. a mixture of sodium hydroxide and sodium acetate.

Suitable acids are all acids which are soluble in the reaction medium. As this is preferably polar protic, acids are preferred which are soluble in polar protic solvents. Examples include mineral acids, such as hydrochloric acid, hydrobromic acid, nitric acid, sulfuric acid, hydrogen sulfate, phosphoric acid or dihydrogen phosphate, carboxylic acids, such as formic acid or acetic acid, and ammonium salts, such as ammonium chloride or ammonium bromide. Among these acids preference is given to use a weaker acid or a combination of different acids comprising at least one weaker acid which can form a buffering system and stabilize the desired pH, such as dihydrogen phosphate, the above carboxylic acids and the above ammonium salts. However if the starting pH is very basic, it is preferred to bring the pH to near the desired pH using a stronger acid, such as the above mineral acids, and then make the fine tuning of the pH with one of the above-listed weaker acids, or to use a mixture of stronger and weaker acids.

The diazonium salt is prepared in acidic medium (see below). Thus, if the adjustment of the pH of the diazonium salt solution desired, this is generally carried out by adding a suitable base, e.g. one of the above listed suitable or preferred bases. Specifically, as in general the diazonium salt is prepared in a strongly acidic medium, it preferred to adjust the pH first with one of the above-listed stronger acids and then make the fine tuning with one of the weaker bases, or to use a mixture of stronger and weaker bases, e.g. a mixture of sodium hydroxide and sodium acetate. However, as already explained, it is not necessary to adjust the pH of the diazonium salt solution.

Formoxime is preferably not used in its commercially available form, but is prepared by reacting a formaldehyde source with hydroxylamine or an acid addition salt of hydroxylamine (see below). As this reaction is generally also carried out in acidic medium, the adjustment of the pH of the formoxime solution is also generally carried out by adding a suitable base, e.g. one of the above listed suitable or preferred bases.

The method of step (ii) corresponds to a Sandmeyer reaction and thus reaction conditions suitable for this reaction type can be applied (see e.g. Organikum, $22^{nd}$ ed., Wiley-VCH, p. 639 et seq.), however with the proviso that the pH is >5.

The reaction in step (ii) is preferably carried out in the presence of a copper (I) salt. This is either a commercially available Cu(I) salt, or is a Cu(I) salt prepared beforehand by reduction of a Cu(II) salt, or is prepared in situ. In this latter case, step (ii) is preferably carried out in the presence of a Cu(II) salt and a reduction agent.

Suitable Cu(I) salts (either commercially available or prepared beforehand) and Cu(II) salts (to be reduced in situ) are preferably those salts which have a sufficient solubility in the solvent system used in step (ii) (see below). As the preferred solvent system is aqueous, it is preferred to use Cu(I) or Cu(II) salts which have a sufficient water-solubility, such as CuCl, $Cu_2SO_4$, $CuNO_3$, $CuCl_2$, $CuSO_4$, $Cu(NO_3)_2$ and the like. Preferably, Cu(I) or (II) sulfate is used.

If the Cu(I) salt is prepared in situ by reduction of Cu(II), the reaction of step (ii) is also carried out in the presence of a reduction agent. In principle all reduction agents can be used which have a sufficient reduction power for converting the Cu(II) cation to the Cu(I) cation under the given reaction conditions but do not reduce other reactants, and which advantageously have a sufficient solubility in the solvent system used. Suitable reduction agents are e.g. sulfite salts, such as sodium or potassium sulfite, dithionite salts, such as sodium or potassium dithionite, thiosulfate salts, such as sodium or potassium thiosulfate, meta-bisulfite salts, such as sodium or potassium meta-bisulfite, hydroxymethanesulfinate salts, such as sodium hydroxymethanesulfinate (Rongalit®) or potassium hydroxymethanesulfinate, $SnCl_2$, Zn and hydrazine. Specifically, sulfite salts are used, and very specifically sodium sulfite is used.

In a preferred embodiment of step (ii), the diazonium salt, preferably in form of a solution, is added to a solution containing formoxime. More preferably, the diazonium salt, preferably in form of a solution, is added to a solution containing the formoxime, a copper salt and, if the copper salt is a Cu(II) salt, also a reduction agent.

Even more preferably, the diazonium salt, preferably in form of a solution, is added to a solution having a pH of >5, preferably a pH of at least 5.1, e.g. 5.1 to 14, preferably 5.1 to 10, e.g. 5.1 to 8 or 5.1 to 7; more preferably a pH of at least 5.2, e.g. 5.2 to 14, preferably 5.2 to 10, e.g. 5.2 to 8 or 5.2 to 7; even more preferably a pH of at least 5.3, e.g. 5.3 to 14, preferably 5.3 to 10, e.g. 5.3 to 8 or 5.3 to 7; and in particular a pH of at least 5.5, e.g. 5.5 to 14, preferably 5.5 to 10, e.g. 5.5 to 8 or 5.5 to 7, and containing formoxime, a copper salt and, if the copper salt is a Cu(II) salt, also a reduction agent. It is not critical whether the adjustment of the pH of the solution containing formoxime, a copper salt and, if the copper salt is a Cu(II) salt, also a reduction agent has been performed before or after the addition of the copper salt and if necessary the reduction agent.

The addition of the diazonium salt (solution) is preferably carried out sequentially, i.e. not in a single portion, but continuously or portionwise. If the diazonium salt solution has not been adjusted to a pH of >5 before being added, it may become necessary to control and adjust the pH of the reaction mixture in the course of the addition. The adjustment of the pH may not be necessary if the diazonium salt solution is not very acidic and/or if a sufficiently strong buffering system has been used for adjusting the pH of the formoxime solution.

Preferably, the diazonium salt, which is preferably used in the form of a solution, is cooled to −10 to +15° C., preferably to −5 to +10° C., more preferably to −5 to +5° C. (the lower value being limited by the solidification point of the solution), before it is reacted with the formoxime, which is preferably also used in form of a solution, more preferably of a solution also containing a copper salt and, if the copper salt is a Cu(II) salt, also a reduction agent.

The temperature of the formoxime solution is not very critical. It is typically in the range of from −10 to +30° C., preferably from 0 to 20° C. and more preferably from 5 to 15° C., the lower value being limited by the solidification point of the solution.

The reaction temperature of step (ii) is generally kept at from −10 to +30° C., preferably from 0 to 20° C. and more preferably from 5 to 15° C. In principle the reaction temperature can be as high as the boiling point of the reaction mixture at the given reaction pressure, but is preferably kept at the indicated lower values in order to allow the control the nitrogen formation (see below).

The reaction pressure is generally not critical and can range from 0.9 to 2 bar, preferably from 0.9 to 1.5 bar and especially from 0.9 to 1.1 bar.

The reaction in step (ii) involves a rather strong gas evolution and foaming originating from nascent nitrogen. Thus the addition of the reactants, e.g. the addition of the diazonium salt (solution) to the formoxime solution, is preferably carried out at such a rate that gas evolution can be controlled. Moreover, the reaction vessel is preferably chosen so that evolving nitrogen can be removed fast.

Formoxime is preferably employed in a molar ratio of from 0.9 to 2 mol, preferably from 0.9 to 1.2 mol and in particular from 0.95 to 1.1, mol per mol of the aniline compound II used in step (i).

The copper salt is preferably used in an amount of from 0.001 to 1 mol, more preferably from 0.001 to 0.2 mol, and in particular from 0.01 to 0.1, mol per mol of aniline compound II used in step (i).

The reduction agent is preferably used in an at least equimolar amount to the amount of Cu(II) salt used. "Equimolar" in this case refers to the number of electrons which the reduction agent can transfer to the Cu(II) cation. For instance, one mol of sulfite salts (in which the sulfur atom passes from oxidation state +IV to oxidation state +VI when reducing Cu(II)) transfers two mole of electrons. Thus in this case the sulfite salt is preferably used in an amount of at least 0.5 mol per mol of Cu(II) salt. More preferably, the reduction agent is used in an amount of from 1 to 5 mol equiv., in particular from 1 to 2 mol equiv. per mol of Cu(II) salt used. Here again mol equiv. refers to the number of electrons which the reduction agent can transfer to the Cu(II) cation (for instance 0.5 mol of a sulfite salt corresponds to 1 mol equiv. of electrons and thus more preferably 0.5 to 2.5 mol, in particular 0.5 to 1 mol of sulfite salt is used per mol of Cu(II) salt).

The reaction of step (ii) is generally carried out under mixing or stirring. The reaction is carried out at least until evolution of nitrogen has ceased.

The oxime compound I formed in step (ii) is isolated from the reaction mixture by customary methods, e.g. by extraction of the reaction mixture with a suitable organic solvent and removal of this solvent or, in case a solvent has been used as reaction medium in which the product is not soluble (e.g. an aqueous solution), by decanting the water phase from the precipitated product and by liberating this from undesired components, e.g. by trituration with a solvent in which the product is not soluble.

Suitable solvents for extraction purposes are essentially immiscible with water and have a sufficient solvation power for compound I. Examples are aliphatic hydrocarbons, such as alkanes, e.g. pentane, hexane or heptane, cycloaliphatic hydrocarbons, such as cycloalkanes, e.g. cyclopentane or cyclohexane, halogenated alkanes, such as methylene chloride or chloroform, aromatic hydrocarbons, such as benzene, toluene, the xylenes or chlorobenzene, open-chained ethers, such as diethylether, methyl-tert-butyl ether or methyl-isobutyl ether, or esters, such as ethyl acetate or ethyl propionate.

Suitable solvents for trituration purposes are polar, e.g. alkanols, such as methanol, ethanol, propanol or isopropanol, lower ketones, such as acetone, lower carboxylic acids, such as acetic acid, or aqueous systems, such as water or acidic aqueous solutions.

The isolated product can be further purified, e.g. by crystallization or by chromatography. However, frequently, the product is already obtained in a purity which does not require further purification steps.

As already indicated above, formoxime is preferably not used in the commercially available form, but is prepared shortly before it is used in reaction step (ii). Its preparation is preferably carried out by reacting a formaldehyde source with hydroxylamine or an acid addition salt thereof.

Suitable formaldehyde sources are e.g. gaseous formaldehyde, formalin, paraformaldehyde or trioxane. For practical reasons, paraformaldehyde is preferably used.

The formaldehyde source (calculated as formaldehyde) and hydroxylamine or its acid addition salt are reacted in a molar ratio of from 0.5:1 to 1:5, preferably from 0.8:1 to 1:1.2, more preferably from 0.9:1 to 1:1.1 and in particular approximately in equimolar amounts.

The reaction is generally carried out in the solvent in which formoxime is to be used in step (ii), i.e. generally in polar protic solvents, such as water, aqueous acidic solutions, $C_1$-$C_3$-alcohols such as methanol, ethanol, propanol and isopropanol, glycols, such as ethylene glycol and diethylene glycol, or mixtures thereof. Preferably water or aqueous acidic solutions are used.

The reaction is preferably carried out under acidic conditions. Suitable acids correspond to those listed above for step (ii). If hydroxylamine is used in form of its acid addition salt, the acidity of the reaction medium is in general sufficient and thus it is not necessary to use a further acid.

The reaction temperature is not critical and can range from the solidifying to the boiling point of the reaction mixture. Preferably it is carried out at elevated temperature, e.g. at from 30° C. to the boiling point of the reaction mixture.

The reaction mixture is preferably not worked up, but is used as such in step (ii), i.e. formoxime is not isolated. Beforehand however, as already explained above, it is preferred to adjust the solution to the desired pH of >5.

Formoxime is preferably prepared shortly before it is used in reaction step (ii). "Shortly before" is not an absolute value, as it depends on several factors like the amount produced, the storing conditions and the like, and might range from a few minutes to several days or even weeks. It is in each case produced so as to insure a reactivity as high as possible.

Step (i) yielding the diazonium salt of following formula

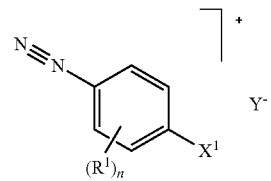

wherein $Y^-$ is a counteranion (equivalent) generally derived from the anion of the acid used in this step corresponds to customary diazotation reactions and thus reaction conditions suitable for this reaction type can be applied (see e.g. Organikum, $22^{nd}$ ed., Wiley-VCH, page 630 et seq.).

The aniline compound II is reacted with a nitrite salt in acidic medium. Alternatively, nitrous acid can be used, but the first variant is preferred.

Suitable nitrites are all salts soluble in the reaction medium. As this is preferably aqueous (see below), preferably water-soluble nitrite salts are used, such as such as lithium nitrite, sodium nitrite or potassium nitrite. Specifically, sodium nitrite is used.

The acidic medium is generally an acidic aqueous solution. Suitable acids are all acids soluble in water and having an anion which does not compete with formoxime in step (ii) as nucleophile. Moreover they should have essentially no oxidation or reduction power. Preferred acids are hydrochloric acid, sulfuric acid or phosphoric acid. Specifically, hydrochloric acid is used.

The acid is generally used in at least equimolar amount with respect to the aniline compound II. "Equimolar amount" in this case refers to the acid equivalents, i.e. to the number of protons which the acid can deliver. For instance, "equimolar amount" in case of sulfuric acid means 0.5 mol of sulfuric acid per mol of aniline compound II (0.5 mol of sulfuric acid can deliver 1 mol of protons). Preferably, 1.1 to 5, more preferably 1.2 to 4 acid equivalents are used per mol of aniline compound II.

Typically, the aniline II is dissolved in water and the acid is added, preferably under cooling so that the temperature preferably does not exceed 50° C. Then the nitrite salt is added, preferably dissolved in water. During addition, the reaction temperature is preferably kept at from −10 to +10° C., more preferably from −5 to +5° C. and in particular from 0 to +5° C., the lower value being limited by the freezing point of the reaction mixture.

In a preferred embodiment, the aniline compound II, before being reacted with the nitrite salt, is recrystallized in an acidic aqueous solution. For example, aniline II is heated in aqueous HCl solution to the boiling point of the solution and is then cooled. The precipitate formed is finely crystalline and has an enhanced reactivity in the diazotation reaction as compared to, for example, commercially available aniline compounds II.

The aniline compound II and the nitrite salt are preferably used in a molar ratio of from 0.5:1 to 1:5, more preferably from 0.8:1 to 1:1.2, even more preferably from 0.9:1 to 1:1.1 and in particular approximately in equimolar amounts.

If desired, at the end of the addition the presence of free nitrous acid can be checked, e.g. with iodide starch paper tests. The reaction is in general considered as terminated if the iodide starch paper does not change its colour for at least 5 minutes. If desired, excess nitrous acid may be removed by addition of sulfamidic acid.

The diazonium salt obtained in step (i) is in general not isolated from the reaction mixture. Instead, the reaction mixture obtained in step (i) is used as such in step (ii), optionally with the above-described adjustment of the pH to the desired pH of at least >5 before it is reacted with formoxime.

Aniline compounds II are either commercially available or can be prepared by standard methods, such as nitration of an aromatic compound

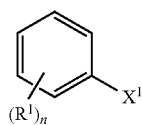

in which $R^1$ is not in the para-position of $X^1$, and subsequent reduction of the nitro group.

Alternatively they can be prepared by p-halogenation of aniline compounds of following formula

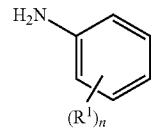

in which $R^1$ is not in the para-position of the amino group.

Methods B and C preferably comprise following further steps (subsequent to steps (i) and (ii)):

(iii-1) reacting the compound of formula I with a compound of formula V

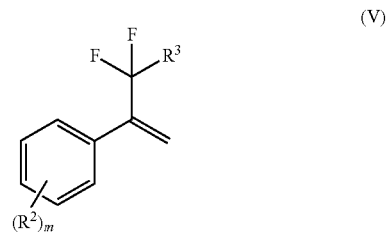

wherein $R^2$, $R^3$ and m as are as defined above, in the presence of a halogenating agent and a base to give a compound of formula III;

or (iii-2a) reacting the compound of formula I with a halogenating agent to give a compound of formula (VI)

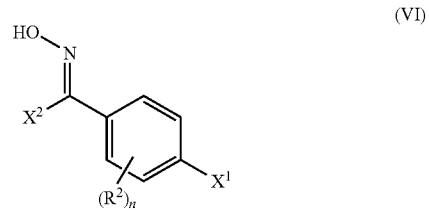

wherein $R^1$, n and $X^1$ are as defined in claim 1 and $X^2$ is a halogen atom;

and (iii-2b) reacting the compound of formula VI obtained in step (iii-2a) with a compound of formula V

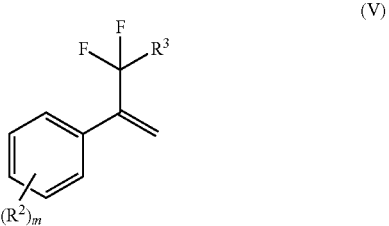

wherein $R^2$, $R^3$ and m as are as defined in claim 2, in the presence of a base to give a compound of formula III.

The ring-closing reaction of step (iii) is principally known e.g. from WO 2007/079162 and WO 2008/145740.

In variant (iii-1) halogenation takes place in situ and the resulting halogenated compound I (=compound VI), due to the presence of a base, is directly reacted with the styrene V in a ring-closing reaction to the isoxazoline compound III.

In variant (iii-2) oxime compound I is first halogenated and only then the halogenated oxime VI is further reacted with or without isolation with compound V in the presence of a base to isoxazoline compound III.

For both variants, halogenating agents for steps (iii-1) or (iii-2a) are preferably selected from chlorine, hypochloric acid, hypochlorite salts, such as sodium hypochlorite; $SbCl_5$, $PCl_5$, $P(O)Cl_3$, $PCl_3$, $S(O)_2Cl_2$ (sulfuryl chloride), $S(O)Cl_2$ (thionyl chloride), N-chlorosuccinimide, bromine, N-bromosuccinimide and N-iodosuccinimide and more preferably from chlorine, hypochloric acid, hypochlorite salts, such as sodium hypochlorite; N-chlorosuccinimide, N-bromosuccinimide and N-iodosuccinimide.

For variant 1 (i.e. for step (iii-1)), more preferred halogenating agents are selected from chlorine, hypochloric acid, hypochlorite salts, such as sodium hypochlorite; N-chlorosuccinimide, N-bromosuccinimide and N-iodosuccinimide and in particular from chlorine, sodium hypochlorite and N-chlorosuccinimide. Specifically N-chlorosuccinimide is used.

For variant 2 (i.e. for step (iii-2a)), more preferred halogenating agents are selected from N-chlorosuccinimide, N-bromosuccinimide and N-iodosuccinimide. Specifically N-chlorosuccinimide is used.

Suitable bases for use in step (iii-1) or (iii-2b) can be organic or inorganic. Examples are hydroxides, such as lithium, sodium or potassium hydroxide, carbonates, such as lithium, sodium or potassium carbonates, hydrogen carbonates, such as lithium, sodium or potassium hydrogen carbonates, phosphates, such as lithium, sodium or potassium phosphate, hydrogen phosphate, such as lithium, sodium or potassium hydrogen phosphate, alkoxides, such as sodium or potassium methoxide, sodium or potassium ethoxide or sodium or potassium tert-butanolate, carboxylates, such as lithium, sodium or potassium formiate, lithium, sodium or potassium acetate or lithium, sodium or potassium propionate, ammonia and amines, such as dimethylamine, trimethylamine, diethylamine, triethylamine, propylamine, dipropylamine, tripropylaime, diisopropylethylamine, diethanolamine, triethanolamine. The choice of the base is not very critical. The base is in general selected so as to be soluble in the solvent system used in step (iii-1) or (iii-2b).

Solvents for step (iii) are preferably polar. Examples of polar protic solvents are water, $C_1$-$C_4$-alkanols, such as methanol, ethanol, propanol, isopropanol, n-butanol, sec-butanol, Isobutanol or tert-butanol, glycols, such as ethylene glycol or diethylene glycol, carboxylic acids, such as acetic acid, and mixtures thereof. Examples of polar aprotic solvents are cyclic ethers, such as tetrahydrofuran or the dioxanes, cyclic or alicyclic amides, such as N,N-dimethylformamide (DMF), N,N-dimethylacetamide or N-methylpyrrolidone, lower nitriles, such as acetonitrile or propionitrile, lower ketones, such as acetone or ethylmethyl ketone, sulfoxides, such as dimethylsulfoxide, and mixtures thereof. Preference is given to the above polar aprotic solvents.

The halogenating agent is preferably employed in a molar ratio of from 0.9 to 10 mol, more preferably from 0.9 to 5 mol and in particular from 0.95 to 2 mol per mol of compound I.

The molar ratio of compounds I and V is preferably in the range of from 1:2 to 2:1, more preferably from 0.8:1.2 to 1.2:0.8 and in particular from 0.9:1.1 to 1.1:0.9.

The base is used in at least equimolar amounts with respect to compound I so as to be able to neutralize the acid HX (X=Cl, Br or I depending on the halogenating agent) formed in the course of step (iii). Preferably, the base is used in an amount of from 1 to 10 mol, more preferably from 1 to 5 mol and in particular from 1 to 2 mol per mol of compound I.

In variant 1 (step (iii-1) it is preferred to first react compound I with the halogenating agent and only then add compound V and the base. Halogenation and ring closing reaction can be carried out at a temperature of from −20 to the boiling point of the reaction mixture. If halogenation is carried out at elevated temperature, i.e. above room temperature, and if the ring closing reaction is to be carried out at a lower temperature, it is preferred to cool the reaction mixture before compound V and the base is added, e.g. to −20 to +20° C. or to −10 to +10° C. The addition sequence of the base and compound V is not critical. However it is preferred to add first compound V and then the base.

In variant 2 (steps iii-2a and -2b) the halogenation step (iii-2a) can be carried out as described above for variant 1. The resulting halogenated oxime VI can be isolated and if desired purified. Isolation can be performed by e.g. first adding water or an aqueous solution to the reaction mixture and then extracting the compound VI with an apolar organic solvent. Suitable solvents are those listed above for extraction of compound I.

The reaction of step (iii-2b) can be carried out by adding for example either styrene V and the base to a solution containing the isolated and optionally purified compound VI, or by adding compound VI to a solution/suspension containing compound V and a base.

The reaction pressure in step (iii) is not critical. Generally the reaction is carried out at ambient pressure. Only in case that chlorine is used as halogenating agent it might be useful to carry out step (iii-1) or (iii-2a) at elevated pressure, e.g. at 1.1 to 5 bar or at 1.2 to 2 bar.

Work-up of the reaction mixture obtained in step (iii) can be carried out in a customary manner.

The reaction mixture obtained in steps (iii-1), (iii-2a) or (iii-2b) is generally subjected to aqueous work-up, e.g. by bringing the reaction mixture into contact with water or an aqueous solution. In case of step (iii-1) or (iii-2b) it may be advantageous to neutralize the reaction mixture, e.g. by using an acidic aqueous solution. The product (compound VI or III) can be isolated via extractive methods, e.g. by extracting the aqueous mixture with an apolar organic solvent and then removing the organic solvent from the separated apolar phase. Suitable apolar solvents are for example those listed above for the extraction of compound I. Further purification can be carried out, for example, by crystallization or by chromatography. However, frequently, the product is already obtained in a purity which does not require further purification steps.

In a preferred embodiment, the styrene compound V used in step (iii) is obtained by reacting a compound of formula VII

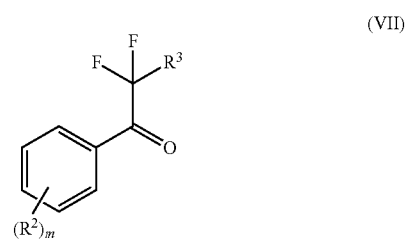

(VII)

wherein $R^2$, $R^3$ and m as are as defined above, with a methylenating agent.

This reaction can be carried out under the reaction conditions of Wittig or Wittig-analogous reactions. Olefination reactions of electron deficient aryl ketones, such as compounds of the formula VII, have been described e.g. by Nader et al, J. Org. Chem. 1994, 59, 2898-2901.

Suitable methylenating agents are all agents known for converting a carbonyl group into an olefinic group.

Preferably, the methylenating agents are selected from dimethyltitanocene (Petasis reagent), diphenylmethylphosphine oxide, dimethoxymethylphosphine sulfide, pentamethylphosphonic diamide, dimethyl sulfoxide, (trialkylstannyl)(trimethylsilyl)-methane, trimethylsilyl(phenylthio)methane, Zn in combination with titanium tetrachloride and diiodomethane or dibromomethane (Lombardo-reagent), dichlorotitanocene and aluminum trimethyl (for preparing the Tebbe reagent), methylenetriphenylphosphine (a Wittig reagent), trimethylsulfonium iodide, dichloro-(cyclopentadienyl)zirconium and diiodomethane or dibromomethane, dimethyl methanephosphonate, methanesulfonyl chloride, (chloromethyl)trimethylsilane, diazomethyltrimethyl silane, Nysted's reagent and precursors of the above methylenating agents.

The choice of the specific methylenating agent depends i.a. on the electronic and steric nature of the residue $R^2$ and its position with respect to the carbonyl group.

More preferably the methylenating agent is obtained in situ or shortly before carrying out the olefination reaction from a precursor of the methylenating agent. Preferably, the precursor is selected from triphenylmethyl phosphinium iodide, triphenylmethyl phosphinium bromide and triphenylmethyl phosphinium chloride, these phosphinium halides being preferably used in freshly powdered form. The resulting methylenating agent is methylenetriphenylphosphine. Especially preferred as precursors are triphenylmethyl phosphinium bromide and triphenylmethyl phosphinium chloride. The precursor is preferably activated by the addition of a base The base for activating the precursor of the methylenating agent is preferably selected from alkali metal alkoxides, such as potassium methoxide, sodium methoxide or potassium tert-butoxide, organolithium reagents, such as methyllithium, butyllithium or phenyllithium, lithium or sodium amides. Preferably alkali metal alkoxides are used. Among these, preference is given to potassium methoxide and sodium methoxide.

The methylenating agent is preferably employed in a molar ratio of from 1 to 1.5, more preferably from 1.02 to 1.2 mol, per mol of compound VII.

The base for activating the precursor is preferably also employed in a molar ratio of from 1 to 1.5 per mol, more preferably from 1.02 to 1.2 mol, per mol of compound VII.

The order of addition of the reagents to the reaction is relatively important as this was found to have an impact on the isolated yield.

In a preferred embodiment, if a precursor of a methylenating agent is used and if the precursor is a phosphonium salt, the precursor, the ketone of formula VII and the solvent are placed together in a reaction vessel and a solution of the base is added subsequently to this mixture. Alternatively the base can also be added in solid form.

The reaction of the ketone VII with a methylenating agent to the styrene V is generally carried out at temperatures of from −78 to 110° C. In general, the upper temperature is limited by the boiling point of the reaction mixture when the reaction is carried out under atmospheric pressure. Preferably the temperature is in the range of from −20° C. to 100° C., more preferably from 0° C. and 80° C. and especially from 20° C. and 70° C.

The reaction pressure is not critical. It is preferably in the range of from 0.9 to 2 bar, particularly preferably from 0.9 to 1.5 bar and especially from 0.9 to 1.1 bar.

The reaction of the compound of formula VII with a methylenating agent is preferably carried out in a suitable solvent. Preferred solvents are aprotic, e.g. aliphatic hydrocarbons, such as pentane, hexane, heptane, octane, nonane and decane, cycloaliphatic hydrocarbons, such as cyclopentane or cyclohexane, aromatic hydrocarbons, such as benzene, toluene, the xylenes, cumene, chlorobenzene, dichlorobenzenes, nitrobenzene, pyridine or tert-butylbenzene, cyclic or acyclic ethers, such as diethyl ether, dipropyl ether, methyl-tert-butyl ether (MTBE), methylisobutyl ether (MIBE), cyclopentyl methyl ether, tetrahydrofuran (THF), methyl THF or the dioxanes (1,3- or preferably 1,4-dioxane), aliphatic nitriles, such as acetonitrile or propionitrile, and mixtures of the solvents mentioned above. Preferably the solvents are used in anhydrous form, which can be obtained by standard drying methods.

Among these, preference is given to aromatic hydrocarbons, such as benzene, toluene, the xylenes, cumene, chlorobenzene, dichlorobenzenes, nitrobenzene, pyridine or tert-butylbenzene, or cyclic or acyclic ethers, such as diethyl ether, dipropyl ether, methyl-tert-butyl ether, methylisobutyl ether, cyclopentyl methyl ether, tetrahydrofuran (THF), methyl THF or the dioxanes. Especially preferred are diethyl ether and THF.

Work-up of the reaction mixture and isolation of the compound of formula V may be carried out in a customary manner, for example by removing the solvent, for example by distillation, by aqueous or extractive work-up or by a combination of these measures.

For example, after completion of the reaction, the solvent may be distilled off and/or a non-polar solvent is added to dissolve the desired product and precipitate the conversion product of the methylenating reagent which is generally scarcely soluble or even insoluble in apolar solvents (e.g. in case of the preferably used methylenetriphenylphosphine or its triphenylphosphine halide precursor, the conversion product is triphenylphosphine oxide). The latter can be filtered off for recycling purposes. Additionally, inorganic salts resulting from the reaction of some of the precursors of the methylenating agents and their activators, e.g. from the reaction of the phosphonium precursor and the base, are also precipitated. Those water-soluble salts can be easily washed off the conversion product of the methylenating agent, e.g. the triphenylphosphine oxide precipitate.

Suitable apolar solvents are for example aliphatic hydrocarbons, such as pentane, hexane or heptane, cycloaliphatic hydrocarbons, such as cyclopentane or cyclohexane, aromatic hydrocarbons, such as benzene, toluene or the xylenes, and open-chained ethers, such as diethyl ether, dipropyl ether, MTBE or MIBE.

The aqueous work-up can for example be carried out by bringing the reaction mixture into contact with water or an aqueous solution. If necessary, the water-containing reaction mixtures obtained in this manner are neutralized. The sytrene compounds of the formula V can for example be isolated by extraction with an organic solvent such as the above-listed apolar solvents, and subsequent removal of the organic solvent. If appropriate, especially when water-miscible solvents are used for the reaction, it may be advantageous to remove at least some of the solvent prior to the extraction, for example by distillation.

Further purification of V can be carried out, for example, by crystallization or by chromatography. However, frequently, the product is already obtained in a purity which does not require further purification steps.

Alternatively the styrene compound V, in the case that the boiling point of the non-polar solvent is higher than the boiling point of the product, can be distilled from the non-polar solvent. In the case of a lower boiling point of the non-polar solvent, the solvent has to be evaporated. The product can then be distilled off from the bottom product.

The keto compound VII used in the Wittig or Wittig-analogous olefination reaction can in turn be prepared for example via a Grignard or Grignard-analogous reaction of a compound VIII

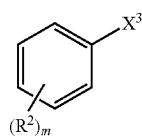

(VIII)

wherein
$X^3$ is Cl, Br or I;
with a carboxylic acid derivative $R^3CF_2$—$C(O)R^a$, wherein $R^a$ is OH, $OC(O)CF_3$, halogen, $C_1$-$C_6$-alkoxy, $N(CH_3)_2$, $N(C_2H_5)_2$, $N(OCH_3)CH_3$, piperidinyl, morpholinyl or piperazinyl, and wherein the last three radicals are bound via their nitrogen atom, and magnesium or another Grignard reagent.

Magnesium can be used in form of turnings or powder. Magnesium can be activated by reagents like iodine, bromine, dibromo ethane or monobromo ethane. Grignard reagents suitable for the reaction are alkyl magnesium halogenides, for example methyl magnesium chloride, methyl magnesium bromide, methyl magnesium iodide, ethyl magnesium chloride, ethyl magnesium bromide, ethyl magnesium iodide, propyl magnesium chloride, propyl magnesium bromide, propyl magnesium iodide, isopropyl magnesium chloride, isopropyl magnesium bromide, isopropyl magnesium iodide, butyl magnesium chloride, butyl magnesium bromide, butyl magnesium iodide, sec-butyl magnesium chloride, sec-butyl magnesium bromide, sec-butyl magnesium iodide, tert-butyl magnesium chloride, tert-butyl magnesium bromide, tert-butyl magnesium iodide, isobutyl magnesium chloride, isobutyl magnesium bromide and isobutyl magnesium iodide.

The reaction is preferably carried out with magnesium, methyl magnesium chloride, methyl magnesium bromide, ethyl magnesium chloride, ethyl magnesium bromide, propyl magnesium chloride, propyl magnesium bromide, isopropyl magnesium chloride, isopropyl magnesium bromide, butyl magnesium chloride, butyl magnesium bromide, sec-butyl magnesium chloride, sec-butyl magnesium bromide, tert-butyl magnesium chloride, tert-butyl magnesium bromide, isobutyl magnesium chloride or isobutyl magnesium bromide.

The reaction is more preferably carried out with magnesium, methyl magnesium chloride, methyl magnesium bromide, isopropyl magnesium chloride, isopropyl magnesium bromide, tert-butyl magnesium chloride or tert-butyl magnesium bromide.

$X^3$ in compound VIII is preferably Cl or Br.

The carboxylic acid derivative $R^3CF_2$—$C(O)R^a$ is selected from di- and trifluoroacetic acid derivatives. Suitable derivatives for the reaction are di- and trifluoroacetyl chlorides, bromides and fluorides as well as di- and trifluoroacetic acid alkylesters, wherein the di- and trifluoroacetic acid alkylesters can be di- and trifluoroacetic acid methyl esters or ethyl esters, further di- and trifluoroacetic acid anhydrides and di- and trifluoroacetamides, especially N,O-dimethylhydroxylamides, dimethylamides, diethylamides, dibutylamides, morpholine amides, piperazine amides and piperidine amides.

Among these, preference is given to di- and trifluoroacetyl chlorides, bromides and fluorides ($R^a$=Cl, Br or F) as well as di- and trifluoroacetic acid alkylesters ($R^a$=$C_1$-$C_6$-alkoxy), di- and trifluoroacetic acid methyl esters and ethyl esters ($R^a$=$OCH_3$ or $OCH_2CH_3$) being preferred.

The Grignard reaction of a compound of the formula VIII with magnesium or a Grignard reagent and the electrophile $R^3CF_2$—$C(O)R^a$ to a compound of formula VII is preferably carried out at temperatures of from −78 to 110° C. In general, the upper temperature is limited by the boiling point of the solvent used under the given reaction pressure. The first step (Grignard reaction) of the reaction is preferably carried out at temperatures of from −30 to 110° C. The second step (electrophile addition) is preferably carried out at temperatures of from −78° C. to 50° C.

In the reaction of compounds of the formula VIII with magnesium or a Grignard reagent (first step) the pressure is preferably in a range of from 0.9 to 2 bar, particularly preferably in a range of from 0.9 to 1.5 bar and especially in a range of from 0.9 to 1.1 bar.

In the reaction of compounds of the first step with the electrophile (second step) the pressure is preferably in a range of from 0.9 to 200 bar, particularly preferably in a range of from 0.9 to 100 bar and especially in a range of from 0.9 to 50 bar.

Magnesium or the Grignard reagent is preferably used in a molar ratio of from 0.9 to 2 mol more preferably from 0.9 to 1.2 mol and in particular from 0.95 to 1.1 mol per mol of compound VIII.

The electropiles are preferably employed in a molar ratio of from 0.9 to 5 mol, more preferably from 0.9 to 2 mol and in particular from 0.95 to 1.5 mol per mol of compound VIII.

The reaction of compound VIII with magnesium or a Grignard reagent and the electrophile can be carried out in organic solvents. Organic solvents suitable for the reaction are aprotic polar and apolar solvents, for example aromatic hydrocarbons, such as benzene, toluene, the xylenes, cumene, chlorobenzene, nitrobenzene, tert-butylbenzene, cyclic or acyclic ethers, such as diethyl ether, dipropyl ether, tert-butyl methyl ether (MTBE), methylisobutyl ether (MIBE), cyclopentyl methyl ether, tetrahydrofuran (THF) or the dioxane (1,3- or 1,4-dioxane, 1,4-dioxane being preferred) or mixtures of the solvents mentioned above.

The reaction mixtures obtained in the reaction of compounds of the formula VII with magnesium or a Grignard reagent and the electrophile $R^3CF_2$—$C(O)R^a$ are generally subjected to aqueous work-up, i.e. the reaction mixture obtained is brought into contact with water or an aqueous acid. After acidification of the water-containing reaction mixtures obtained in this manner, the compounds of the formula VII can generally be isolated by extraction with an organic solvent and subsequent removal of the organic solvent. If appropriate, especially when water-miscible solvents are used for the reaction, it may be advantageous to remove at least some of the solvent prior to the extraction, for example by distillation.

Further purification can be carried out, for example, by crystallization or by chromatography. However, frequently, the product is already obtained in a purity which does not require further purification steps.

Compounds of formula VIII are either commercially available or can be produced by standard methods.

Method C preferably comprises following further reaction step (iv) (subsequent to step (iii)):

(iv) reacting the compound of formula III obtained in step (iii-1) or (iii-2b) with CO and an amine or formula NHR$^8$R$^9$ in the presence of a palladium catalyst, where R$^8$ and R$^9$ are as defined above, to give a compound of formula IV.

The reaction of a compound of the formula III with carbon monoxide and an amine to a compound of formula IV is preferably carried out at temperatures of from −20 to 140° C. In general, the upper temperature is limited by the boiling point of the solvent in question when the reaction is carried out under atmospheric pressure.

The reaction pressure is preferably in a range of from 0.9 to 100 bar, particularly preferably in a range of from 0.9 to 50 bar and especially in a range of from 0.9 to 20 bar.

The amine NHR$^8$R$^9$ is preferably employed in a molar ratio of from 0.8 to 5 mol, more preferably from 0.9 to 2 mol and in particular from 0.95 to 1.5 mol per mol of compound III.

The reaction is performed in the presence of a suitable Pd catalyst.

Suitable palladium catalysts for the reaction of the compounds of the formula III with CO and amines are palladium-containing compounds in which the palladium has an oxidation state of 0 or 2.

Examples of palladium-containing compounds having an oxidation state of 0 are palladium(0) ligand complexes, such as palladium(0)tetrakis(triphenylphosphine), palladium(0)tetrakis(diphenylmethylphosphine) or palladium(0)-bis (DIPHOS), or metallic palladium which may be supported, if appropriate. Metallic palladium is preferably applied to an inert support, such as activated carbon, alumina, barium sulfate, barium carbonate or calcium carbonate. The reaction in the presence of metallic palladium is preferably carried out in the presence of suitable complex ligands.

Examples of palladium-containing compounds having an oxidation state of 2 are palladium(II) ligand complexes, such as palladium(II) acetylacetonate, or compounds of the formula PdX$_2$L$_2$ in which X is halogen and L is a monovalent ligand, in particular a ligand of the formula (A) or (B) shown below, and also palladium(II) salts, such as, for example, palladium acetate or palladium chloride, preferably palladium chloride.

If palladium(II) salts are used, the reaction is preferably carried out in the presence of suitable complex ligands, especially the complex ligands of the formulae (A) and (B) shown below.

The palladium catalyst may be employed in the form of a finished palladium complex or as a palladium compound which, under the reaction conditions, forms, as a precatalyst, the catalytically active compound together with suitable ligands.

Suitable complex ligands for the reaction of compounds of the formula III with CO and amines are, for example, mono- or bidentate phosphines of the formulae (A) and (B) shown below

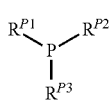

(A)

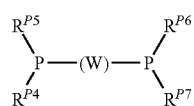

(B)

in which R$^{P1}$ to R$^{P7}$ are independently of one another C$_1$-C$_6$-alkyl, C$_5$-C$_8$-cycloalkyl, adamantyl, aryl-C$_1$-C$_2$-alkyl or, preferably, ferrocenyl or aryl which may optionally be substituted by C$_1$-C$_4$-alkyl or C$_1$-C$_4$-alkoxy, and W is a straight-chain bivalent hydrocarbon group having preferably 2 to 5 carbon atoms which is unsubstituted or optionally substituted, where the bivalent hydrocarbon group may be part of a mono- or bicyclic ring which for its part is unsubstituted or may have further substituents.

A in the compounds of the formulae (A) and (B) is especially C$_1$-C$_4$-alkylene, C$_0$-C$_1$-alkyleneferrocenyl, 1,1'-biphenyl-2,2'-diyl or 1,1'-binaphthyl-2,2'-diyl, where the four last-mentioned groups may optionally be substituted by C$_1$-C$_4$-alkyl or C$_1$-C$_4$-alkoxy and where C$_1$-C$_4$-alkylene may additionally have one or more substituents selected from the group consisting of C$_3$-C$_7$-cycloalkyl, aryl and benzyl. In this context, aryl is naphthyl or optionally substituted phenyl. Aryl is preferably phenyl or tolyl, particularly preferably phenyl. C$_0$-C$_1$-Alkyleneferrocenyl is especially ferrocenediyl, where the two phosphorus atoms are in each case attached to one cyclopentadiene of the ferrocene, or is methyleneferrocenyl, where one of the phosphorus atoms is attached via the methylene group to a cyclopentadiene, the second phosphorus atom is attached to the same cyclopentadiene and the methylene group may optionally have 1 or 2 further substituents selected from C$_1$-C$_4$-alkyl.

The complex ligands used in the process for reacting compounds of the formula III with CO and amines are preferably bidentate phosphines, such as 1,3-bis(diphenylphosphino) propane (DPPP), 1,3-bis(diphenylphosphino)ethane, 1,3-bis (dicyclohexylphosphino)propane (DCPP), ferrocenyl-containing phosphines of the JosiPhos type, 1,1'-bis (diphenylphosphino)ferrocene (DPPF) or 2,2-dimethyl-1,3-bis(diphenylphosphino)propane and particularly preferably DPPF.

The catalyst is preferably employed in a molar ratio of from 0.00001 mol to 0.1 mol, more preferably from 0.0001 mol to 0.05 mol per mol of compound III.

The reaction is preferably performed in the presence of a suitable base.

Suitable bases are inorganic bases, such as potassium hydroxide, sodium hydroxide, lithium hydroxide, potassium carbonate, sodium carbonate, lithium carbonate, potassium hydrogencarbonate, sodium hydrogencarbonate, lithium hydrogencarbonate, potassium phosphate or sodium phosphate, as well as certain organic bases which show sufficient basicity but no nucleophility, such as tertiary amines, e.g. trimethylamine, triethylamine, tripropylamine, diisopropylethylamine, triethanolamine or N-methylpiperidine, basic aromatic N-heterocycles, such as pyridine, 4-dimethylaminopyridine, the picolines (2-methylpyridine α-picoline), 3-methylpyridine (β-picoline), 4-methylpyridine (γ-picoline)), the lutidines (2,3-dimethylpyridine (2,3-lutidine), 2,4-dimethylpyridine (2,4-lutidine), 2,5-dimethylpyridine (2,5-lutidine), 2,6-dimethylpyridine (2,6-lutidine), 3,4-dimethylpyridine (3,4-lutidine), 3,5-dimethylpyridine (3,5-lutidine)), or the collidines (2,3,4-trimethylpyridine (2,3,4-collidine), 2,3,5-trimethylpyridine (2,3,5-collidine), 2,3,6-trimethylpyridine (2,3,6-collidine), 2,4,5-trimethylpyridine (2,4,5-collidine), 2,4,6-trimethylpyridine (2,4,6-collidine), 3,4,5-trimethylpyridine (3,4,5-collidine)), and bicyclic non-nucleophilic amines such as 1,4-diazabicyclo[2.2.2]octane, 1,8-diazabicyclo[5.4.0]undec-7-ene (DBU) or 1,5-diazabicyclo[4.3.0]non-5-ene (DBN). Among the inorganic bases, preference is given to using potassium carbonate or potassium phosphate. Among the organic bases, preference is given to the tertiary amines, pyridine and DBU.

Preferably, the base should be essentially water-free. This can be achieved by usual means, e.g. by heating the inorganic bases or the solid organic bases, preferably under vacuum, or by distilling the liquid organic bases over anhydrous potassium hydroxide, potassium carbonate, calcium hydride or sodium.

The base is preferably employed in a molar ratio of from 0.5 to 100 mol, more preferably from 0.9 to 10 mol and in particular from 0.95 to 5 mol per mol of compound III.

Inorganic bases are preferably employed in an amount of at least one, particularly preferably 1 to 4 and especially about 2 molar equivalents, based on the amount of the isoxazoline compound of the formula III used.

Organic bases are preferably employed in an amount of from 0.1 to 4, preferably from 0.2 to 0.7 molar equivalents, based on the amount of the isoxazoline compound of the formula III used.

Organic solvents suitable for the reaction are for example aromatic hydrocarbons, such as benzene, toluene, the xylenes, cumene, chlorobenzene, nitrobenzene, pyridine or tert-butylbenzene, halogenated hydrocarbons, such as dichloromethane, chloroform, tetrachloromethane, 1,2-dichloroethane, 1,1,1-trichloroethane, cyclic or acyclic ester, such as ethyl acetate or gamma butyrolactone, acyclic ethers, such as diethyl ether, dipropyl ether, tert-butyl methyl ether (MTBE), isobutylmethylether or ethyleneglycol dimethylether (DME), aprotic polar solvents, for example cyclic ethers, such as tetrahydrofuran (THF) or the dioxanes (1,3- or 1,4-dioxane, 1,4-dioxane being preferred), cyclic or acyclic amides, such as dimethylformamide, dimethylacetamide, N-methylpyrrolidone or tetramethylurea, aliphatic nitriles, such as acetonitrile or propionitrile, lower ketones, such as acetone, or DMSO, and also mixtures of the solvents mentioned above or mixtures of the solvents mentioned above and water.

The reaction is however preferably carried out in aprotic solvents, preferably in cyclic or acyclic ethers, such as diethyl ether, dipropyl ether, tert-butyl methyl ether (MTBE), isobutylmethyl ether (MIBE), tetrahydrofuran (THF) or dioxane, cyclic or acyclic amides, such as dimethylformamide, dimethylacetamide, N-methylpyrrolidone or tetramethylurea, or aliphatic nitriles, such as acetonitrile or propionitrile, aromatic hydrocarbons, such as benzene, toluene, the xylenes, cumene, chlorobenzene, nitrobenzene, pyridine or tert-butylbenzene and also mixtures of the solvents mentioned above or mixtures of the solvents mentioned above and water.

The solvent used is preferably essentially water-free, i.e. the solvent has a water content of less than 1000 ppm and in particular not more than 100 ppm.

This is generally achieved by usual means, e.g. by distilling the solvent over a suitable drying agent, such as calcium hydride, sodium, potassium, molar sieve, phosphorpentoxide and the like.

The reaction mixture obtained in the reaction of compounds of the formula III with CO and an amine is generally subjected to aqueous work-up, i.e. it is brought into contact with water or an aqueous solution. After neutralization of the water-containing reaction mixtures obtained in this manner, the compounds of the formula IV can generally be isolated by extraction with an organic solvent and subsequent removal of the organic solvent. If appropriate, especially when water-miscible solvents are used for the reaction, it may be advantageous to remove at least some of the solvent prior to the extraction, for example by distillation.

Further purification can be carried out, for example, by crystallization or by chromatography. However, frequently, the product is already obtained in a purity which does not require further purification steps.

In the above compounds (i.e. in compounds I, II, III, IV, VI and the diazonium salt obtained in step (i)) n is 1 or 2 and specifically 1.

If n is 1, $R^1$ is preferably bound in ortho position to the group $X^1$ in compounds I, II, III, VI and the diazonium salt or in ortho position to the carboxamido group $C(O)NR^8R^9$ in compound IV.

$R^1$ in the above compounds (i.e. compounds I, II, III, VI and the diazonium salt) is preferably selected from F, Cl, CN, $NO_2$, $SF_5$, $C_1$-$C_6$-alkyl, $C_1$-$C_6$-haloalkyl, $C_1$-$C_6$-alkoxy, $C_1$-$C_6$-haloalkoxy and $C_1$-$C_4$-alkoxy-$C_1$-$C_4$-alkyl, more preferably from F, Cl, CN, $NO_2$, $SF_5$, $C_1$-$C_4$-alkoxy and $C_1$-$C_4$-haloalkoxy, even more preferably from $CH_3$, $CF_3$, $CH_2CH_3$, $CH_2CF_3$, Cl, CN, $NO_2$, $SF_5$, $OCH_3$, $OCF_3$ and $OCHF_2$, specifically from CN, Cl, $OCH_3$ and $CH_3$ and very specifically from Cl, $OCH_3$ and $CH_3$.

m in the above compounds (i.e. in compounds III, IV, V, VII and VIII) is preferably 1, 2 or 3, more preferably 2 or 3.

If m is 1, $R^2$ is preferably bound in 3-position with respect to the 1-position of the attachment point of the phenyl ring to the isoxazoline ring in compounds III and IV or with respect to the 1-position of the group —C(=$CH_2$)$CF_2R^3$ in compound V or with respect to the 1-position of the group —C(O)$CF_2R^3$ in compound VII or with respect to the 1-position of $X^3$ in compound VIII.

If m is 2, the two radicals $R^2$ are preferably bound in 3,5-position with respect to the 1-position of the attachment point of the phenyl ring to the isoxazoline ring in compounds III and IV or with respect to the 1-position of the group —C(=$CH_2$)$CF_2R^3$ in compound V or with respect to the 1-position of the group —C(O)$CF_2R^3$ in compound VII or with respect to the 1-position of $X^3$ in compound VIII.

If m is 3, the three radicals $R^2$ are preferably bound in 3,4,5-position with respect to the 1-position of the attachment point of the phenyl ring to the isoxazoline ring in compounds III and IV or with respect to the 1-position of the group —C(=$CH_2$)$CF_2R^3$ in compound V or with respect to the 1-position of the group —C(O)$CF_2R^3$ in compound VII or with respect to the 1-position of $X^3$ in compound VIII.

$R^2$ in the above compounds (i.e. in compounds III, IV, V, VII and VIII) is preferably selected from F, Cl, cyano, $C_1$-$C_6$-alkyl, $C_1$-$C_8$-haloalkyl, $C_1$-$C_6$-alkoxy and $C_1$-$C_8$-haloalkoxy, more preferably from F, Cl, cyano, $C_1$-$C_4$-haloalkyl, $C_1$-$C_4$-alkoxy and $C_1$-$C_4$-haloalkoxy, even more preferably from F, Cl, cyano, $C_1$-$C_4$-alkyl and $C_1$-$C_4$-haloalkyl, in particular from F, Cl, CN and $CF_3$, and specifically from Cl and $CF_3$.

Particularly, the compound of formula V is a compound of formula V.1

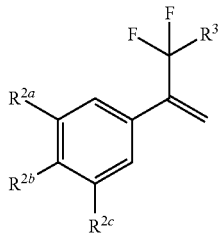
(V.1)

where $R^{2a}$, $R^{2b}$ and $R^{2c}$ are hydrogen or have one of the general meanings or, in particular, one of the preferred meanings given above for $R^2$.

Accordingly, compounds VII and VIII are in a particular embodiment compounds of formulae VII.1 and VIII.1

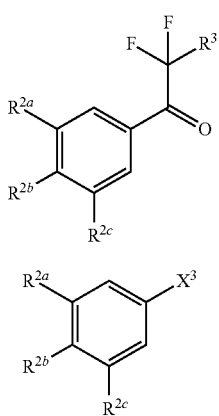

(VII.1)

(VIII.1)

and compounds III and IV are in a particular embodiment compounds of formulae III.1 and IV.1

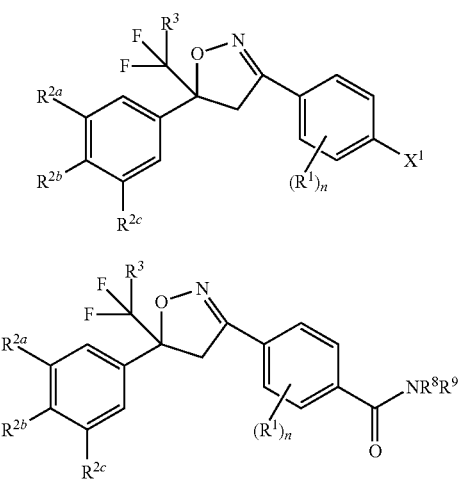

(III.1)

(IV.1)

where $R^{2a}$, $R^{2b}$ and $R^{2c}$ are hydrogen or have one of the general meanings or, in particular, one of the preferred meanings given above for $R^2$.

In the above compounds III.1, IV.1, V.1, VII.1 and VIII.1 preferably $R^{2a}$ is selected from H, F, Cl and $CF_3$;
$R^{2b}$ is selected from H, F, Cl and CN; and
$R^{2c}$ is selected from H, F, Cl and $CF_3$.

$R^3$ in the above compounds (i.e. compounds III, IV, V and VII), is preferably selected from H, F, Cl and $CF_3$ and is specifically F.

The invention is now illustrated by the following non-limiting examples.

EXAMPLES

The compounds can be characterized e.g. by coupled High Performance Liquid Chromatography/mass spectrometry (HPLC/MS), by $^1$H-NMR and/or by their melting points.

Analytical HPLC column: RP-18 column Chromolith Speed ROD from Merck KgaA, Germany). Elution: acetonitrile+0.1% trifluoroacetic acid (TFA)/water+0.1% trifluoroacetic acid (TFA) in a ratio of from 5:95 to 95:5 in 5 minutes at 40° C.

$^1$H-NMR. The signals are characterized by chemical shift (ppm) vs. tetramethylsilane, by their multiplicity and by their integral (relative number of hydrogen atoms given). The following abbreviations are used to characterize the multiplicity of the signals: m=multiplett, q=quartett, t=triplett, d=doublet and s=singulett.

TABLE C.1

Compound examples (Comp. ex.)

| Comp. ex. no. | Structure |
|---|---|
| 1 | 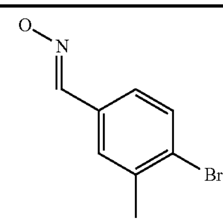 |
| 2 | 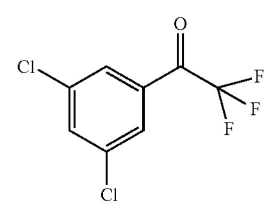 [SMILES: O=C(c1cc(Cl)cc(Cl)c1)C(F)(F)F] |
| 3 | 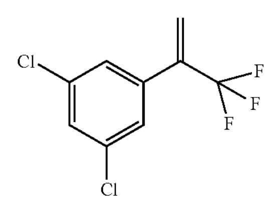 |
| 4 | 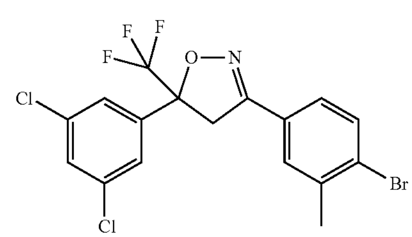 [SMILES: Cc1cc(C2=NOC(c3cc(Cl)cc(Cl)c3)(C(F)(F)F)C2)ccc1Br] |

TABLE C.1-continued

Compound examples (Comp. ex.)

| Comp. ex. no. | Structure |
|---|---|
| 5 | 5-(3,5-dichlorophenyl)-5-(trifluoromethyl)-3-[4-methyl-3-(pyridin-2-ylmethylcarbamoyl)phenyl]-4,5-dihydroisoxazole |
| 6 | 4-bromo-3-chlorobenzaldehyde oxime |
| 7 | 2-bromo-5-[(hydroxyimino)methyl]benzonitrile |
| 8 | 1-(3,4,5-trichlorophenyl)-2,2,2-trifluoroethanone |
| 9 | 1-(3-chlorophenyl)-2,2,2-trifluoroethanone |
| 10 | 2,2,2-trifluoro-1-[3-(trifluoromethyl)phenyl]ethanone |
| 11 | 1,1,1-trifluoro-2-[3-(trifluoromethyl)phenyl]prop-2-ene |
| 12 | 1-[3,5-bis(trifluoromethyl)phenyl]-2,2,2-trifluoroethanone |
| 13 | 1,2,3-trichloro-5-(3,3,3-trifluoroprop-1-en-2-yl)benzene |
| 14 | 1-chloro-3-(3,3,3-trifluoroprop-1-en-2-yl)benzene |
| 15 | 1,3-bis(trifluoromethyl)-5-(3,3,3-trifluoroprop-1-en-2-yl)benzene |
| 16 | 3-(4-bromo-3-chlorophenyl)-5-(3,5-dichlorophenyl)-5-(trifluoromethyl)-4,5-dihydroisoxazole |
| 17 | 3-(4-bromo-3-methylphenyl)-5-(3-chlorophenyl)-5-(trifluoromethyl)-4,5-dihydroisoxazole |

TABLE C.1-continued

Compound examples (Comp. ex.)

| Comp. ex. no. | Structure |
|---|---|
| 18 | 3-[3,5-bis(trifluoromethyl)phenyl]-3-(trifluoromethyl)-5-(4-bromo-3-methylphenyl)-4,5-dihydroisoxazole structure |
| 19 | 3-[3-(trifluoromethyl)phenyl]-3-(trifluoromethyl)-5-(4-bromo-3-methylphenyl)-4,5-dihydroisoxazole structure |
| 20 | 3-(3,4,5-trichlorophenyl)-3-(trifluoromethyl)-5-(4-bromo-3-methylphenyl)-4,5-dihydroisoxazole structure |
| 21 | 1-(3,5-dichlorophenyl)-2,2-difluoroethan-1-one structure |
| 22 | 1-(3,5-dichlorophenyl)-2-fluoro-prop-1-ene (with CHF) structure |

SYNTHESIS EXAMPLES

Example S.1

Synthesis of 4-bromo-3-methyl-benzaldehyde oxime

Solution No. 1:

Paraformaldehyde (5.4 g, 180 mmol) was added to 140 ml of water in a 250 ml reaction flask as well as hydroxylamine hydrochloride (12.5 g, 180 mmol). The reaction mixture was heated (90° C. bath temperature) until it became a clear solution. After cooling to room temperature sodium acetate was added (40.8 g, 497 mmol) and the mixture was again heated to reflux for 10 minutes. The pH of the solution was 5.5.

Solution No. 2:

Into a 500 ml four-necked reaction flask fitted with a mechanical stirrer and a condenser was placed 4-bromo-3-methyl-phenylamine (22.3 g, 120 mmol), 40 ml of water and 80 g of crashed ice. Hydrochloric acid (45.6 ml) was added with cooling (ca.-10° C.) as well as a solution of sodium nitrite (8.3 g, 120 mmol) in 20 ml of water dropwise at such a rate that the reaction mixture did not exceed a temperature of +5° C. During addition the reaction was vigorously stirred with a mechanical stirrer. After the reaction mixture was allowed to be stirred for additional 15 minutes at the same temperature a solution of sodium acetate (22 g, 268 mmol) was added resulting in a solution of a final pH value of about 4.10 (checked by a pH glass-electrode). This second solution was stirred for another 10-15 minutes at 5-10° C. before it was used in the reaction with solution no. 1 (see below).

Solution no. 1 was transferred into a 4-necked 2-liter reaction flask equipped with a condenser and a mechanical stirrer and treated with a solution comprising copper sulphate pentahydrate (3.0 g, 12 mmol), sodium sulfite (0.44 g, 3.5 mmol) and sodium acetate (132 g, 1610 mmol) in water (220 ml) at 10-15° C. Solution no. 2 was added slowly. During the addition the reaction mixture was foaming which limited the addition rate, but could be minimized by intensive stirring. Throughout the addition of solution no. 2 the pH was monitored and maintained above 5. After addition the reaction mixture was allowed to come slowly to room temperature and stirring was continued for about 2 hours. At the end of the reaction the pH of the resulting mixture was still above 5.

Work-up: Dichloromethane (ca. 500 ml) was added with stirring. The phases were allowed to separate and the organic phase was washed with hydrochloric acid (10%) and sodium hydroxide solution (10%) as well as water. After drying over sodium sulphate the solvent was evaporated in vacuo to give a crude oil which was triturated with methanol (ca. 100 ml). The precipitating solid was filtered off and the remainder concentrated in vacuo to yield upon standing a solid, non-sticky, flowable product (19.2 g, 75% yield).

HPLC-MS: 2.925 min, M=213.8

$^1$H-NMR (360 MHz, DMSO): δ=2.35 (s, 3H), 7.34 (m, 1H), 7.60 (m, 2H), 8.10 (s, 1H), 11.33 (s, 1H) ppm.

Example S.2

Synthesis of 3,5-dichloro-2,2,2-trifluoro acetophenone (Compound Example No. 2 of Table C.1)

To 5.1 g (0.209 mol) of magnesium turnings were added 0.45 g of a 1 molar solution of DIBAL in hexane at 60° C. After 15 min, 3,5-dichloro-bromobenzene (5.0 g, 0.022 mol) and 25 mL THF were added and the mixture was stirred. After start up of the reaction a mixture of 45 g (0.2 mol) 3,5-dichloro-bromobenzene and 250 mL THF was added under reflux. After completion of the reaction the mixture was cooled to 0° C. and 31.1 g (0.219 mol) of ethyl trifluoroacetate were added. After 2 h an aqueous solution of NH$_4$Cl was added and the mixture was separated between MTBE and aqueous NH$_4$Cl solution. The organic layer was separated and the solvent was removed in vacuum. (34.3 g brown oil; purity 70% acc. to g.c.; yield 50%)

$^1$H-NMR (360 MHz, CDCl$_3$): δ=7.7 (s, 1H), 7.9 (s, 2H) ppm.

In the manner described different electrophiles were used:

| | |
|---|---|
| Trifluoroacetyl chloride: | Yield: 36% |
| Trifluoroacetyl fluoride: | Yield: 10% |
| N,O-dimethylhydroxyl-amid of trifluoro acetic acid: | Yield: 26%. |

Example S.3

Synthesis of 1,3-dichloro-5-(1-trifluoromethyl-vinyl)-benzene (Compound Example No. 3 of Table C.1)

To a suspension of methyl-triphenylphosphonium iodide in THF was added KOtBu (0.620 g, 5.54 mmol) at room temperature. After 30 min, 3,5-dichloro-2,2,2-trifluoro acetophenone (1.20 g, 4.94 mmol) from example S.2 was added and the mixture was stirred over night. The mixture was separated between MTBE and aqueous $NH_4Cl$ solution. The organic layer was separated and the solvent was removed in vacuum. Column chromatography on $SiO_2$ with cyclohexane gave the title compound (0.73 g, 61%).

$^1$H-NMR (360 MHz, $CDCl_3$): δ=5.82 (s, 1H), 6.06 (s, 1H), 7.32 (s, 2H), 7.38 (s, 1H) ppm.

Example S.4

Synthesis of 1,3-dichloro-5-(1-trifluoromethyl-vinyl)-benzene (Compound Example No. 3 of Table C.1)

To a suspension of methyl-triphenylphosphonium iodide (161.7 g, 0.450 mol) and 3,5-dichloro-2,2,2-trifluoro acetophenone (100 g, 0.390 mol) from example S.2 in THF (650 mL) was added a solution of KOtBu (55.4 g, 0.490 mol) in THF (280 mL) at 20-25° C. within 20 min. After 1.5 h at room temp, the mixture was separated between heptane and water. The organic layer was washed with 1% aqueous NaCl solution, then the solvent was removed in vacuum. The residue was triturated in n-heptane and filtered over a plug of silica. The filtrate was evaporated to give the title compound (69.00 g, 73%) as an oil (purity 95% acc. to g.c).

$^1$H-NMR (360 MHz, $CDCl_3$): δ=5.82 (s, 1H), 6.06 (s, 1H), 7.32 (s, 2H), 7.38 (s, 1H) ppm.

Example S.4.1

Synthesis of 1,3-dichloro-5-(1-trifluoromethyl-vinyl)-benzene (Compound Example No. 3 of Table C.1)

To a suspension of methyl-triphenylphosphonium bromide (1637.4 g, 4.50 mol) and 3,5-dichloro-2,2,2-trifluoro acetophenone (941 g, 3.90 mol) from example S.2 in THF (9000 mL) was added a solution of KOtBu (554.7 g, 4.90 mol) in THF (4500 mL) at 18-19° C. within 3 h. After 5 h at room temp, 7500 mL solvent was distilled off under reduced pressure at 48° C., 400 mbar. N-heptane (5000 mL) was added to the reaction mixture and cooled to 10° C. The precipitate was filtered off and the filter cake was washed with 4000 mL n-heptane. The filtrate was evaporated to give the title compound. After distillation the product was obtained (620.00 g, 66%) as an oil (purity 99% acc. to g.c).

Example S.4.2

Synthesis of 1,3-dichloro-5-(1-trifluoromethyl-vinyl)-benzene (Compound Example No. 3 of Table C.1)

To a suspension of methyl-triphenylphosphonium bromide (11.3 g, 0.03 mol) and 3,5-dichloro-2,2,2-trifluoro acetophenone (10 g, (purity 65%) 0.026 mol) in THF (97 mL) was added a suspension of KOMe (2.49 g, 0.033 mol) in THF (55 mL) at 18-20° C. within 15 min. After 5 h at room temp, 76 mL solvent was distilled off under reduced pressure 48° C., 400 mbar. N-heptane 100 mL was added to the reaction mixture and cooled to 10° C. The precipitate was filtered off and the filter cake was washed with 100 mL of n-heptane. The filtrate was evaporated to give the title compound, (10.8 g, 80%) as an oil (purity 47% acc. to g.c).

Example S.4.3

Synthesis of 1,3-dichloro-5-(1-trifluoromethyl-vinyl)-benzene (Compound Example No. 3 of Table C.1)

To a suspension of methyl-triphenylphosphonium chloride (9.9 g, 0.03 mol) and 3,5-dichloro-2,2,2-trifluoro acetophenone (10.0 g, purity 65%, 0.026 mol) in THF (97 mL) was added a suspension of KOMe (2.49 g, 0.033 mol) in THF (55 mL) at 18-20° C. within 15 min. After 5 h at 50° C., 76 mL solvent was distilled off under reduced pressure 48° C., 400 mbar. N-heptane 100 mL was added to the reaction mixture and cooled to 10° C. The precipitate was filtered off and the filter cake was washed with 100 mL of n-heptane. The filtrate was evaporated to give the title compound, (10.2 g, 71%) as an oil (purity 45% acc. to g.c).

Example S.4.4

Synthesis of 1,3-dichloro-5-(1-trifluoromethyl-vinyl)-benzene (Compound Example No. 3 of Table C.1)

To a suspension of methyl-triphenylphosphonium bromide (10.51 g) and 3,5-dichloro-2,2,2-trifluoro acetophenone (10.0 g, purity 65%) in THF (35 mL) was added a suspension of NaOMe (1.73 g) in THF (35 mL) at 20° C. After 1.5 h at room temp and 30 min at 50° C., the reaction was complete by GC. N-heptane 100 mL was added to the reaction mixture and cooled to 10° C. The precipitate was filtered off and the filter cake was washed with 100 mL of n-heptane. The filtrate was evaporated to give the title compound, (9.35 g, 74%) as an oil (purity 51% acc. to g.c).

$^1$H-NMR (360 MHz, $CDCl_3$): δ=5.82 (s, 1H), 6.06 (s, 1H), 7.32 (s, 2H), 7.38 (s, 1H) ppm.

Example S.5

Synthesis of 3-(4-bromo-3-methyl-phenyl)-5-(3,5-dichloro-phenyl)-5-trifluoromethyl-4,5-dihydro-isoxazole (Compound Example No. 4 of Table C.1)

To a solution of 4-bromo-3-methyl-benzaldehyde oxime (2.600 g, 12.15 mmol) from example S.1 in DMF (40 mL) was added N-chloro succinimide (1.700 g, 12.73 mmol) and the mixture was heated at 70° C. (bath temperature) for 1 h. After cooling to 0° C., a solution of 1,3-dichloro-5-(1-trifluoromethyl-vinyl)-benzene (2.900 g, 12.03 mmol) in DMF (8 mL), followed by triethylamine (2.00 g, 2.75 mL, 19.8 mmol) was added. After 1 h at this temperature, the cooling bath was removed and the mixture was stirred over night. The mixture was separated between MTBE and aqueous NH$_4$Cl solution. The organic layer was separated and the solvent was removed in vacuum. Column chromatography on SiO$_2$ with heptane/CH$_2$Cl$_2$ gave the title compound (2.95 g, 54%).

HPLC-MS (long method): 4.248 min, M=452.05

Example S.6

Synthesis of 3-(4-bromo-3-methyl-phenyl)-5-(3,5-dichloro-phenyl)-5-trifluoromethyl-4,5-dihydro-isoxazole (Compound Example No. 4 of Table C.1)

To a solution of 4-bromo-3-methyl-benzaldehyde oxime (11.13 g, 52.00 mmol) from example S.1 in DMF (50 mL) was added N-chloro succinimide (7.29 g, 54.6 mmol) and the mixture was heated at 75° C. (bath temperature) for 1 h. After cooling, ice-water was added and the mixture was extracted with MTBE. The combined organic layers were sequentially washed with water and brine, dried over Na$_2$SO$_4$ and evaporated. The residue was dissolved in THF (50 mL) and added to a suspension of 1,3-dichloro-5-(1-trifluoro-methyl-vinyl)-benzene (15.60 g, 51.78 mmol) and KHCO$_3$ (9.63 g, 96.2 mmol) in THF (25 mL). The resulting mixture was heated at reflux temperature for 20 h. After cooling, water was added and the mixture was extracted with EtOAc. The combined organic layers were dried and the solvent was removed in vacuum. Column chromatography on SiO$_2$ with heptane/CH$_2$Cl$_2$ gave the title compound (20.00 g, 85%).

HPLC-MS (long method): 4.248 min, M=452.05

Example S.7

Synthesis of 4-[5-(3,5-dichloro-phenyl)-5-trifluoromethyl-4,5-dihydro-isoxazol-3-yl]-2-methyl-N-pyridin-2-ylmethyl-benzamide (Compound Example No. 5 of Table C.1)

A mixture of 3-(4-bromo-3-methyl-phenyl)-5-(3,5-dichloro-phenyl)-5-trifluoromethyl-4,5-dihydro-isoxazole (1.02 g, 2.24 mmol), 2-picolylamine (369 mg, 3.41 mmol), Pd(dppf)C$_{12}$ (92 mg, 0.13 mmol) triethylamine (5.2 mL, 3.8 g. 37 mmol) and DMF (50 mL) was flushed with carbon monoxide and stirred under an atmosphere of CO at 100° C. for 26 h. The solvent was removed in vacuum and the residue was taken up in EtOAc, filtered and evaporated. The residue was chromatographed on SiO$_2$ to give the title compound (391 mg, 34%).

HPLC-MS: 3.414 min, M=508.10

Example S.8

Synthesis of 1,3-dichloro-5-(1-trifluoromethyl-vinyl)-benzene (Compound Example No. 3 of Table C.1)

To a suspension of methyl-triphenylphosphonium bromide (16.17 g, 25.27 mmol) and 3,5-dichloro-2,2,2-trifluoro acetophenone (10.0 g, 41.15 mmol) in THF (65 mL) was added KOtBu (5.54 g, 49.38 mmol) in THF (28 mL) at 20-25° C. After 1.5 h at room temp, the reaction was complete by GC. The mixture was separated between n-heptane and water. The organic layer was separated, washed with brine and the solvent was removed in vacuum. After cooling, the mixture was filtered from precipitating triphenylphosphine oxide to yield the title compound (8.78 g, 79%).

$^1$H-NMR (360 MHz, CDCl$_3$): δ=5.82 (s, 1H), 6.06 (s, 1H), 7.32 (s, 2H), 7.38 (s, 1H) ppm.

Example S.9

Synthesis of 3-(4-bromo-3-methyl-phenyl)-5-(3,5-dichloro-phenyl)-5-trifluoromethyl-4,5-dihydro-isoxazole (Compound Example No. 4 of Table C.1)

Chlorine gas was bubbled through a suspension of 4-bromo-3-methyl-benzaldehyde oxime (4.00 g) in ethyl acetate (30 mL) for 1 h. The temperature during the reaction did rise to 40° C. After this time, nitrogen was bubbled through the mixture to remove residual chlorine gas. Then, 1,3-dichloro-5-(1-trifluoro-methyl-vinyl)-benzene (4.26 g) was added and triethylamine (6.9 mL, 5.0 g) in ethyl acetate (15 mL) was added dropwise and the mixture was stirred at room temperature over night. After that, aqueous Na—HCO$_3$ solution (10%) was added, and the organic layer was extracted with ethyl acetate. The combined organic layers were dried and the solvent was removed in vacuum. Column chromatography on SiO$_2$ with heptane/CH$_2$Cl$_2$ gave the title compound (4.96 g, 65%).

HPLC-MS (long method): 4.248 min, M=452.05

Example S.10

Synthesis of 3-(4-bromo-3-methyl-phenyl)-5-(3,5-dichloro-phenyl)-5-trifluoromethyl-4,5-dihydro-isoxazole (Compound Example No. 4 of Table C.1)

To a solution of 4-bromo-3-methyl-benzaldehyde oxime (97.00 g, purity 90% acc. to GC) in DMF (450 mL) was added N-chloro succinimide (57.18 g) and the mixture was heated at 80° C. (bath temperature) for 1 h. After cooling, ice-water was added and the mixture was extracted with MTBE. The combined organic layers were sequentially washed with water and brine, dried over Na$_2$SO$_4$ and evaporated. The residue was dissolved in THF (300 mL) and added to a suspension of 1,3-dichloro-5-(1-trifluoromethyl-vinyl)-benzene (102.40 g) and KHCO$_3$ (75.52 g) in THF (600 mL). The resulting mixture was heated at reflux temperature for 20 h. After cooling, water was added and the mixture was extracted with EtOAc. The combined organic layers were washed with 2 M HCl, and water, dried and the solvent was removed in vacuum. The residue was triturated with cold diisopropyl ether to yield the title compound (124.3 g) as a solid. From the mother liquid, further amounts of the title compound (29.6 g) were collected after concentration and precipitation with n-heptane. Total yield 153.90 g, 83%.

HPLC-MS (long method): 4.248 min, M=452.05

Example S.11

Synthesis of 1,3-dichloro-5-(1-difluoromethyl-vinyl)-benzene (Compound Example No. 22 of Table C.1)

To a suspension of methyl-triphenylphosphonium bromide (1.75 g) and 3,5-dichloro-2,2-difluoro acetophenone (1.0 g) in THF (6.5 mL) was added KOtBu (0.60 g) in THF (2.8 mL) at 20-25° C. After 1.5 h at room temp, the reaction was complete by GC. The mixture was separated between n-heptane and water. The organic layer was separated, washed with brine and the solvent was removed in vacuum. After cooling, the mixture was taken up in n-heptane and filtered over a plug of silica gel. After evaporation of the solvent the title compound (0.58 g, 58%) was obtained as an oil (purity 98.9% acc. to g.c).

$^1$H-NMR (360 MHz, CDCl$_3$): δ=5.76 (m, 2H), 6.32 (t, 1H), 7.38 (m, 3H) ppm.

We claim:

1. A method for preparing a compound of formula (III)

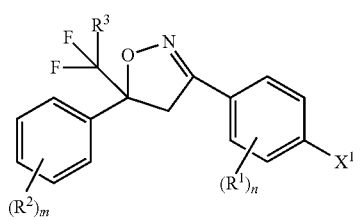

(III)

wherein each R$^1$ is independently selected from the group consisting of F, Cl, CN, NO$_2$, SF$_5$, C$_1$-C$_6$-alkyl, C$_1$-C$_6$-haloalkyl, C$_3$-C$_8$-cycloalkyl, C$_3$-C$_8$-halocycloalkyl, C$_3$-C$_8$-cycloalkyl-C$_1$-C$_4$-alkyl, C$_3$-C$_8$-halocycloalkyl-C$_1$-C$_4$-alkyl, C$_1$-C$_6$-alkoxy, C$_1$-C$_6$-haloalkoxy, C$_1$-C$_4$-alkoxy-C$_1$-C$_4$-alkyl, C$_3$-C$_8$-cycloalkoxy, phenyl and a 3-, 4-, 5-, 6- or 7-membered saturated, partially unsaturated or completely unsaturated heterocyclic ring with 1, 2 or 3 heteroatoms or heteroatom groups selected from N, O, S, NO, SO and SO$_2$, as ring members, where phenyl or the heterocyclic ring may carry 1, 2 or 3 substituents selected from F, Cl, CN, NO$_2$, SF$_5$, C$_1$-C$_6$-alkyl, C$_1$-C$_6$-haloalkyl, C$_3$-C$_8$-cycloalkyl, C$_3$-C$_8$-halocycloalkyl, C$_3$-C$_8$-cycloalkyl-C$_1$-C$_4$-alkyl, C$_3$-C$_8$-halocycloalkyl-C$_1$-C$_4$-alkyl, C$_1$-C$_6$-alkoxy, C$_1$-C$_6$-haloalkoxy and C$_1$-C$_4$-alkoxy-C$_1$-C$_4$-alkyl;

each R$^2$ is independently selected from the group consisting of F, Cl, cyano, azido, nitro, —SCN, SF$_5$, C$_1$-C$_6$-alkyl, C$_1$-C$_6$-haloalkyl, C$_3$-C$_8$-cycloalkyl, C$_3$-C$_8$-halocycloalkyl, —OR$^4$, —Si(R$^5$)$_2$R$^6$, phenyl which may be substituted by 1, 2, 3, 4 or 5 radicals R$^7$, and a 3-, 4-, 5-, 6- or 7-membered saturated, partially unsaturated or completely unsaturated heterocyclic ring containing 1, 2 or 3 heteroatoms or heteroatom groups selected from the group consisting of N, O, S, NO, SO and SO$_2$, as ring members, where the heterocyclic ring may be substituted by one or more radicals R$^7$;

R$^3$ is selected from the group consisting of H, F, Cl or CF$_3$;

R$^4$ is selected from the group consisting of C$_1$-C$_6$-alkyl, C$_1$-C$_6$-haloalkyl, C$_3$-C$_8$-cycloalkyl, C$_3$-C$_8$-cycloalkyl-C$_1$-C$_4$-alkyl, phenyl which may be substituted by 1, 2, 3, 4 or 5 radicals R$^7$, and a 3-, 4-, 5-, 6- or 7-membered saturated, partially unsaturated or completely unsaturated heterocyclic ring containing 1, 2 or 3 heteroatoms or heteroatom groups selected from the group consisting of N, O, S, NO, SO and SO$_2$, as ring members, where the heterocyclic ring may be substituted by one or more radicals R$^7$;

R$^5$, R$^6$ are, independently of each other and independently of each occurrence, selected from the group consisting of C$_1$-C$_4$-alkyl, C$_3$-C$_6$-cycloalkyl, C$_1$-C$_4$-alkoxy-C$_1$-C$_4$-alkyl, phenyl and benzyl;

each R$^7$ is independently selected from the group consisting of F, Cl, cyano, azido, nitro, —SCN, SF$_5$ and C$_1$-C$_{10}$-alkyl which may be partially or fully halogenated;

X$^1$ is selected from the group consisting of Br and I and, in case that R$^1$ is not Cl or phenyl which carries one or more substituents F or Cl or a heterocyclic ring which carries one or more substituents F or Cl, X$^1$ may also be Cl;

m is 0, 1, 2 or 3; and n is 1 or 2;

comprising:

(i) reacting a compound of formula (II)

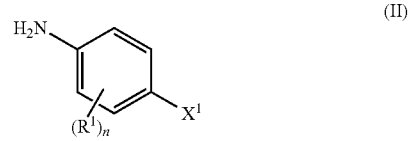

(II)

with a nitrite salt in an acidic medium to form a diazonium salt;

(ii) reacting the diazonium salt obtained in step (i) with formoxime CH$_2$=N—OH in the presence of a copper salt, where step (ii) is carried out at a pH of more than 5, to a compound of formula (I)

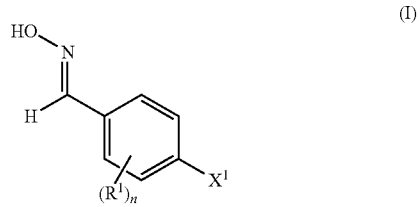

(I)

(iii-1) reacting the compound of formula (I) with a compound of formula (V)

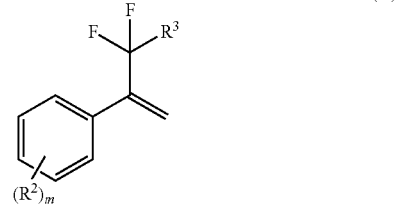

(V)

in the presence of a halogenating agent and a base to give a compound of formula (III); or (iii-2a) reacting the compound of formula (I) with a halogenating agent to give a compound of formula (VI)

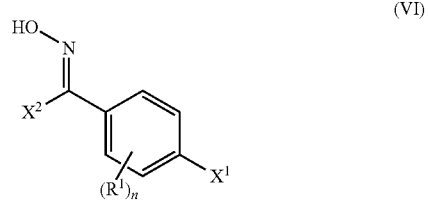

(VI)

wherein X$^2$ is a halogen atom; and (iii-2b) reacting the compound of formula (VI) obtained in step (iii-2a) with the compound of formula (V)

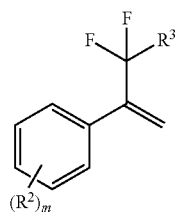

(V)

in the presence of a base to give the compound of formula (III).

2. A method for preparing a compound of formula (IV)

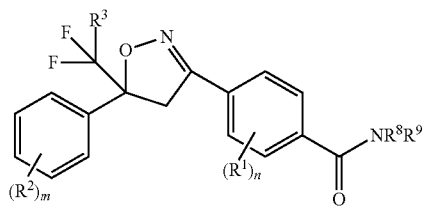

(IV)

wherein each $R^1$ is independently selected from the group consisting of F, Cl, CN, $NO_2$, $SF_5$, $C_1$-$C_6$-alkyl, $C_1$-$C_6$-haloalkyl, $C_3$-$C_8$-cycloalkyl, $C_3$-$C_8$-halocycloalkyl, $C_3$-$C_8$-cycloalkyl-$C_1$-$C_4$-alkyl, $C_3$-$C_8$-halocycloalkyl-$C_1$-$C_4$-alkyl, $C_1$-$C_6$-alkoxy, $C_1$-$C_6$-haloalkoxy, $C_1$-$C_4$-alkoxy-$C_1$-$C_4$-alkyl, $C_3$-$C_8$-cycloalkoxy, phenyl and a 3-, 4-, 5-, 6- or 7-membered saturated, partially unsaturated or completely unsaturated heterocyclic ring with 1, 2 or 3 heteroatoms or heteroatom groups selected from N, O, S, NO, SO and $SO_2$, as ring members, where phenyl or the heterocyclic ring may carry 1, 2 or 3 substituents selected from F, Cl, CN, $NO_2$, $SF_5$, $C_1$-$C_6$-alkyl, $C_1$-$C_6$-haloalkyl, $C_3$-$C_8$-cycloalkyl, $C_3$-$C_8$-halocycloalkyl, $C_3$-$C_8$-cycloalkyl-$C_1$-$C_4$-alkyl, $C_3$-$C_8$-halocycloalkyl-$C_1$-$C_4$-alkyl, $C_1$-$C_6$-alkoxy, $C_1$-$C_6$-haloalkoxy and $C_1$-$C_4$-alkoxy-$C_1$-$C_4$-alkyl;

each $R^2$ is independently selected from the group consisting of F, Cl, cyano, azido, nitro, —SCN, $SF_5$, $C_1$-$C_6$-alkyl, $C_1$-$C_6$-haloalkyl, $C_3$-$C_8$-cycloalkyl, $C_3$-$C_8$-halocycloalkyl, —$OR^4$, —$Si(R^5)_2R^6$, phenyl which may be substituted by 1, 2, 3, 4 or 5 radicals $R^7$, and a 3-, 4-, 5-, 6- or 7-membered saturated, partially unsaturated or completely unsaturated heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^7$;

$R^3$ is selected from the group consisting of H, F, $C_1$ or $CF_3$;

$R^4$ is selected from the group consisting of $C_1$-$C_6$-alkyl, $C_1$-$C_6$-haloalkyl, $C_3$-$C_8$-cycloalkyl, $C_3$-$C_8$-cycloalkyl-$C_1$-$C_4$-alkyl, phenyl which may be substituted by 1, 2, 3, 4 or 5 radicals $R^7$, and a 3-, 4-, 5-, 6- or 7-membered saturated, partially unsaturated or completely unsaturated heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^7$;

$X^1$ is selected from the group consisting of Br and I and, in case that $R^1$ is not Cl or phenyl which carries one or more substituents F or Cl or a heterocyclic ring which carries one or more substituents F or Cl, $X^1$ may also be Cl;

m is 0, 1, 2 or 3;

n is 1 or 2;

$R^8$ is selected from H, $C_1$-$C_6$-alkyl which may carry 1, 2, 3 or 4 substituents $R^{10}$, and Z-A, wherein Z is a chemical bond, $CH_2$, $CH_2CH_2$ or C=O;

A is selected from the group consisting of

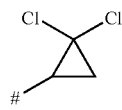 A-1

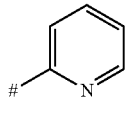 A-2

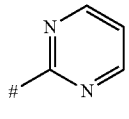 A-3

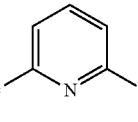 A-4

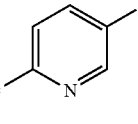 A-5

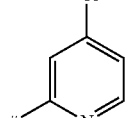 A-6

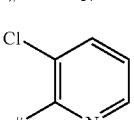 A-7

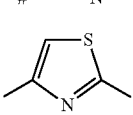 A-8

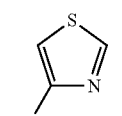 A-9

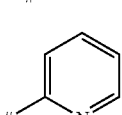 A-10

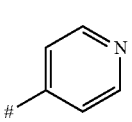 A-11

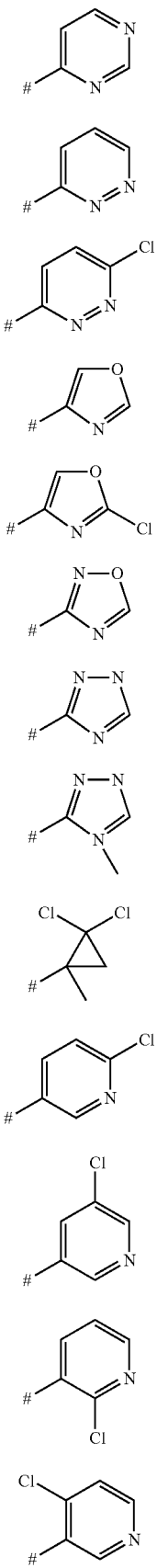

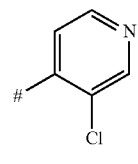

and wherein the "#" in the formulae of variables A indicate the attachment point to Z;

each $R^{10}$ is independently selected from the group consisting of halogen, cyano, azido, nitro, —SCN, $SF_5$, $C_1$-$C_6$-alkyl, $C_1$-$C_6$-haloalkyl, $C_1$-$C_6$-alkoxy-$C_1$-$C_6$-alkyl, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, —Si($R^{17}$)$_2$$R^{18}$, —$OR^{11}$, —$OSO_2R^{11}$, —$SR^{11}$, —$S(O)_mR^{11}$, —$S(O)_nN(R^{12})R^{13}$, —$N(R^{12})R^{13}$, —$C(=O)N(R^{12})R^{13}$, —$C(=S)N(R^{12})R^{13}$, —$C(=O)OR^{11}$, phenyl which may be substituted by 1, 2, 3, 4 or 5 radicals $R^{14}$, and a 3-, 4-, 5-, 6- or 7-membered saturated, partially unsaturated or completely unsaturated heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^{14}$;

or two geminally bound radicals $R^{10}$ together form a group selected from the group consisting of =$CR^{15}R^{16}$, =$S(O)_mR^{11}$, =$S(O)_mN(R^{12})R^{13}$, =$NR^{12}$, =$NOR^{11}$ and =$NNR^{12}$;

or two radicals $R^{10}$, together with the carbon atoms to which they are bound, form a 3-, 4-, 5-, 6-, 7- or 8-membered saturated or partially unsaturated carbocyclic or heterocyclic ring containing 1, 2 or 3 heteroatoms or heteroatom groups selected from the group consisting of N, O, S, NO, SO and $SO_2$, as ring members;

wherein $R^{11}$ is selected from the group consisting of hydrogen, cyano, $C_1$-$C_6$-alkyl, $C_2$-$C_6$-alkenyl, $C_2$-$C_6$-alkynyl, and $C_3$-$C_8$-cycloalkyl, wherein the four last mentioned radicals may be unsubstituted, partially or fully halogenated and/or wherein one or two $CH_2$ groups may be replaced by a CO group; and/or may carry 1 or 2 radicals selected from the group consisting of $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_1$-$C_6$-alkoxycarbonyl, trimethylsilyl, triethylsilyl, tert-butyldimethylsilyl, phenyl, benzyl, pyridyl and phenoxy;

it being possible for phenyl, benzyl, pyridyl and phenoxy to be unsubstituted, partially or fully halogenated and/or to carry 1, 2 or 3 substituents selected from the group consisting of $C_1$-$C_6$-alkyl, $C_1$-$C_6$-haloalkyl, $C_1$-$C_6$-alkoxy, $C_1$-$C_6$ haloalkoxy and $C_1$-$C_6$-alkoxycarbonyl;

$R^{12}$, $R^{13}$ are, independently from one another, selected from the group consisting of hydrogen, cyano, $C_1$-$C_6$-alkyl, $C_2$-$C_6$-alkenyl, $C_2$-$C_6$-alkynyl, and $C_3$-$C_8$-cycloalkyl, wherein the four last mentioned radicals may be unsubstituted, partially or fully halogenated and/or wherein one or two $CH_2$ groups may be replaced by a CO group;

and/or may carry 1 or 2 radicals selected from the group consisting of $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_1$-$C_6$-alkoxycarbonyl, trimethylsilyl, triethylsilyl, tert-butyldimethylsilyl, phenyl, benzyl, pyridyl and phenoxy, it being possible for phenyl, benzyl, pyridyl and phenoxy to be unsubstituted, partially or fully halogenated and/or to carry 1, 2 or 3 substituents selected from the group consisting of $C_1$-$C_6$-alkyl, $C_1$-$C_6$-haloalkyl, $C_1$-$C_6$-alkoxy, $C_1$-$C_6$ haloalkoxy and $C_1$-$C_6$-alkoxycarbonyl;

or, $R^{12}$ and $R^{13}$, together with the nitrogen atom to which they are bound, form a 3-, 4-, 5-, 6- or 7-membered saturated, partly unsaturated or completely unsaturated heterocyclic ring which may contain 1 or 2 further heteroatoms selected from the group consisting of N, O and S as ring members, where the heterocyclic ring may carry 1, 2, 3 or 4 substituents selected from the group consisting of halogen, $C_1$-$C_4$-alkyl, $C_1$-$C_4$-haloalkyl, $C_1$-$C_4$-alkoxy and $C_1$-$C_4$-haloalkoxy;

each $R^{14}$ is, independently of each occurrence and independently from one another, selected from the group consisting of hydrogen, cyano, $C_1$-$C_6$-alkyl, $C_2$-$C_6$-alkenyl, $C_2$-$C_6$-alkynyl and $C_3$-$C_8$-cycloalkyl, where the four last-mentioned radicals may be unsubstituted, partially or fully halogenated and/or wherein one or two $CH_2$ groups may be replaced by a CO group, and/or may carry 1 or 2 radicals selected from the group consisting of $C_1$-$C_4$-alkoxy, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_1$-$C_6$-alkoxycarbonyl trimethylsilyl, triethylsilyl, tert-butyldimethylsilyl, phenyl, benzyl, pyridyl and phenoxy, it being possible for phenyl, benzyl, pyridyl and phenoxy to be unsubstituted, partially or fully halogenated and/or to carry 1, 2 or 3 substituents selected from the group consisting of $C_1$-$C_6$-alkyl, $C_1$-$C_6$-haloalkyl, $C_1$-$C_6$-alkoxy, $C_1$-$C_6$ haloalkoxy and $C_1$-$C_6$-alkoxycarbonyl;

or two radicals $R^{14}$ together form a group =$C(C_1$-$C_4$-alkyl$)_2$, =$N(C_1$-$C_6$-alkyl), =$NO(C_1$-$C_6$-alkyl); or =O;

or, two radicals $R^{14}$ bound to the same nitrogen atom, together with this nitrogen atom form a 3-, 4-, 5-, 6- or 7-membered saturated, partly unsaturated or completely unsaturated ring which may contain 1 or 2 further heteroatoms selected from the group consisting of N, O and S as ring members, where the heterocyclic ring may carry 1 or 2 substituents selected from the group consisting of halogen atoms, $C_1$-$C_4$-alkoxy and $C_1$-$C_4$-haloalkoxy;

$R^{15}$, $R^{16}$ are, independently from one another, selected from the group consisting of hydrogen, halogen, cyano, azido, nitro, —SCN, $SF_5$, $C_1$-$C_6$-alkyl, $C_2$-$C_6$-alkenyl, $C_2$-$C_6$-alkynyl and $C_3$-$C_8$-cycloalkyl, where the four last mentioned radicals may be unsubstituted, partially or fully halogenated and/or oxygenated, and/or may carry 1 or 2 radicals selected from the group consisting of $C_1$-$C_4$-alkyl; $C_1$-$C_4$-haloalkyl; $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tert-butyldimethylsilyl, —OH, —SH, phenyl, benzyl, pyridyl and phenoxy, it being possible for phenyl, benzyl, pyridyl and phenoxy to be unsubstituted, partially or fully halogenated and/or to carry 1, 2 or 3 substituents selected from the group consisting of $C_1$-$C_6$-alkyl, $C_1$-$C_6$-haloalkyl, $C_1$-$C_6$-alkoxy, $C_1$-$C_6$ haloalkoxy; ($C_1$-$C_6$-alkoxy)carbonyl, ($C_1$-$C_6$-alkyl)amino, and di-($C_1$-$C_6$-alkyl)amino;

or $R^{15}$ and $R^{16}$ together form a group =$C(C_1$-$C_4$-alky$)_2$, =$N(C_1$-$C_6$-alky), =$NO(C_1$-$C_6$-alky), or =O;

$R^{17}$, $R^{18}$ are, independently of each other, selected from the group consisting of $C_1$-$C_4$-alkyl, $C_3$-$C_6$-cycloalkyl, $C_1$-$C_4$-alkoxy-$C_1$-$C_4$-alkyl, phenyl and benzyl;

and $R^9$ is selected from the group consisting of H, $CH_3$, $CH_2CH_3$, $CH_2CH_2CH_3$, C(=O)$CH_3$ and C(=O)$OCH_3$;

comprising:

(i) reacting a compound of formula (II)

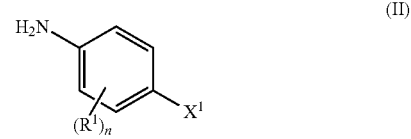

wherein each $R^1$ is independently selected from the group consisting of F, Cl, CN, $NO_2$, $SF_5$, $C_1$-$C_6$-alkyl, $C_1$-$C_6$-haloalkyl, $C_3$-$C_8$-cycloalkyl, $C_3$-$C_8$-halocycloalkyl, $C_3$-$C_8$-cycloalkyl-$C_1$-$C_4$-alkyl, $C_3$-$C_8$-halocycloalkyl-$C_1$-$C_4$-alkyl, $C_1$-$C_6$-alkoxy, $C_1$-$C_6$-haloalkoxy, $C_1$-$C_4$-alkoxy-$C_1$-$C_4$-alkyl, $C_3$-$C_8$-cycloalkoxy, phenyl and a 3-, 4-, 5-, 6- or 7-membered saturated, partially unsaturated or completely unsaturated heterocyclic ring with 1, 2 or 3 heteroatoms or heteroatom groups selected from N, O, S, NO, SO and $SO_2$, as ring members, where phenyl or the heterocyclic ring may carry 1, 2 or 3 substituents selected from F, Cl, CN, $NO_2$, $SF_5$, $C_1$-$C_6$-alkyl, $C_1$-$C_6$-haloalkyl, $C_3$-$C_8$-cycloalkyl, $C_3$-$C_8$-halocycloalkyl, $C_3$-$C_8$-cycloalkyl-$C_1$-$C_4$-alkyl, $C_3$-$C_8$-halocycloalkyl-$C_1$-$C_4$-alkyl, $C_1$-$C_6$-alkoxy, $C_1$-$C_6$-haloalkoxy and $C_1$-$C_4$-alkoxy-$C_1$-$C_4$-alkyl;

$X^1$ is selected from the group consisting of Br and I and, in case that $R^1$ is not Cl or phenyl which carries one or more substituents F or Cl or a heterocyclic ring which carries one or more substituents F or Cl, $X^1$ may also be Cl;
n is 1 or 2;
with a nitrite salt in an acidic medium to a diazonium salt; and
(ii) reacting the diazonium salt obtained in step (i) with formoxime $CH_2=N-OH$ in the presence of a copper salt, where step (ii) is carried out at a pH of more than 5, to give a compound of formula (I)

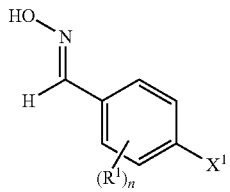

(I)

(iii-1) reacting the compound of formula (I) with a compound of formula (V)

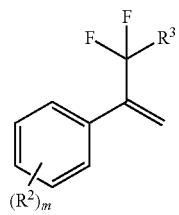

(V)

wherein
each $R^2$ is independently selected from the group consisting of F, Cl, cyano, azido, nitro, —SCN, $SF_5$, $C_1$-$C_6$-alkyl, $C_1$-$C_6$-haloalkyl, $C_3$-$C_8$-cycloalkyl, $C_3$-$C_8$-halocycloalkyl, —$Si(R^5)_2R^6$, phenyl which may be substituted by 1, 2, 3, 4 or 5 radicals $R^7$, and a 3-, 4-, 5-, 6- or 7-membered saturated, partially unsaturated or completely unsaturated heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^7$;
$R^3$ is selected from the group consisting of H, F, $C_1$ or $CF_3$; and
m is 0, 1, 2 or 3;
in the presence of a halogenating agent and a base to give a compound of formula (III)

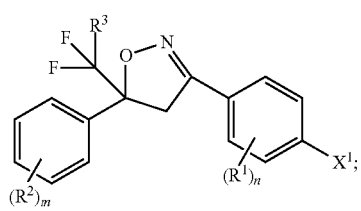

(III);

or
(iii-2a) reacting the compound of formula (I) with a halogenating agent to give a compound of formula (VI)

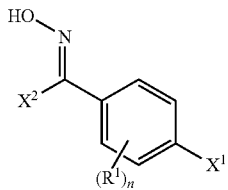

(VI)

wherein $X^2$ is a halogen atom;
and
(iii-2b) reacting the compound of formula (VI) obtained in step (iii-2a) with a compound of formula (V)

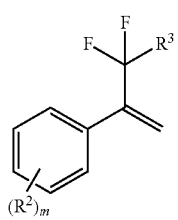

(V)

in the presence of a base to give a compound of formula (III);
and
(iv) reacting the compound of formula (III) obtained in step (iii-1) or (iii-2b) with CO and an amine or formula $NHR^8R^9$ in the presence of a palladium catalyst, where $R^8$ and $R^9$ are as defined above, to give a compound of formula (IV).

3. The method as claimed in claim 1, where step (ii) is carried out at a pH of at least 5.1.

4. The method as claimed in claim 3, where step (ii) is carried out at a pH of 5.1 to 14.

5. The method as claimed in claim 1, where step (ii) is carried out in the presence of a Cu(I) salt.

6. The method as claimed in claim 5, where the Cu(I) salt is generated in situ by carrying out step (ii) in the presence of a Cu(II) salt and a reduction agent.

7. The method as claimed in claim 5, where the reduction agent is selected from the group consisting of sulfite salts, dithionite salts, thiosulfate salts, meta-bisulfite salts, hydroxymethanesulfinate salts, $SnCl_2$, Zn and hydrazine.

8. The method as claimed in claim 1, where in step (ii) the diazonium salt is added to a solution containing the formoxime, a copper salt and, if the copper salt is a Cu(II) salt, also a reduction agent.

9. The method as claimed in claim 8, where the diazonium salt is cooled to −10 to +15° C. before being added to the solution containing the formoxime, a copper salt and, if the copper salt is a Cu(II) salt, also a reduction agent.

10. The method as claimed in claim 8, where the solution containing the formoxime, a copper salt and, if the copper salt is a Cu(II) salt, also a reduction agent, is adjusted to a pH of >5, before the diazonium salt is added.

11. The method as claimed in claim 1, where in the course of the reaction of step (ii) the pH is controlled continuously or periodically and if necessary adjusted to a pH of >5.

12. The method as claimed in claim 1, where the adjustment of the pH is performed by using a system which comprises a buffering agent.

13. The method as claimed in claim 12, where the adjustment of the pH is performed by using at least one base which comprises an acetate salt.

14. The method as claimed in claim 2, where the formoxime used in step (ii) is prepared before step (ii) by reacting formaldehyde or a formaldehyde source with hydroxylamine or an acid addition salt thereof.

15. The method as claimed in claim 3, where the aniline compound of formula II, before being reacted with the nitrite salt, is recrystallized in an acidic aqueous solution.

16. The method as claimed in claim 4, where the halogenating agent used in step (iii-1) or (iii-2a) is selected from the group consisting of chlorine, hypochloric acid, hypochlorite salts, $SbCl_5$, $PCl_5$, $P(O)Cl_3$, $PCl_3$, $S(O)_2Cl_2$ (sulfuryl chloride), $S(O)Cl_2$ (thionyl chloride), N-chlorosuccinimide, bromine, N-bromosuccinimide and N-iodosuccinimide.

17. The method as claimed in claim 1, where the compound of formula V is obtained by reacting a compound of formula VII

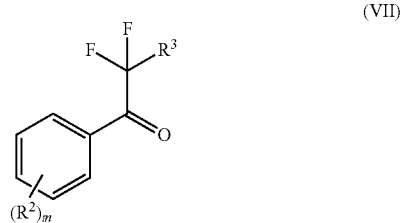

wherein $R^2$, $R^3$ and m as are as defined in claim 2,
with a methylenating agent.

18. The method as claimed in claim 17, where the methylenating agent is selected from the group consisting of dimethyltitanocene, diphenylmethylphosphine oxide, dimethoxymethylphosphine sulfide, pentamethylphosphonic diamide, dimethyl sulfoxide, (trialkylstannyl)(trimethylsilyl)methane, trimethylsilyl(phenylthio)methane, titanium tetrachloride and diiodomethane or dibromomethane, dichlorotitanocene and aluminum trimethyl, methylenetriphenylphosphine, trimethylsulfonium iodide, dichloro(cyclopentadienyl)zirconium and diiodomethane or dibromomethane dimethyl methanephosphonate, methanesulfonyl chloride, (chloromethyl)trimethylsilylane, diazomethyltrimethyl silane, Nysted's reagent and precursors of the above methylenating agents.

19. The method as claimed in claim 18, where the methylenating agent is methylenetriphenylphosphine.

20. The method as claimed in claim 19, where methylenetriphenylphosphine is prepared from triphenylmethyl phosphinium iodide, triphenylmethyl phosphinium bromide or triphenylmethyl phosphinium chloride in situ or shortly before the reaction of compound VII with the methylenating agent is carried out.

21. The method as claimed in claim 17, where compound of formula VII is prepared by reacting a compound VIII

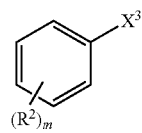

wherein
$R^2$ and m are as defined in claim 1; and
$X^3$ is Cl, Br or I;
with a carboxylic acid derivative $R^3CF_2$—$C(O)R^a$, wherein
$R^3$ is as defined in claim 1 and
$R^a$ is OH, $OC(O)CF_3$, halogen, $C_1$-$C_6$-alkoxy, $N(CH_3)_2$, $N(C_2H_5)_2$, $N(OCH_3)CH_3$, piperidinyl, morpholinyl or piperazinyl, wherein the last three radicals are bound via their nitrogen atom,
and magnesium or another Grignard reagent.

22. The method as claimed in claim 1, where in case that n is 1, $R^1$ is bound in ortho position to the group $X^1$ in compounds I, II, III and VI or in ortho position to the carboxamido group $C(O)NR^8R^9$ in compound IV.

23. The method as claimed in claim 1, where $R^1$ is selected from the group consisting of $CH_3$, $CF_3$, $CH_2CH_3$, $CH_2CF_3$, Cl, Br, I, CN, $NO_2$, $SF_5$, $OCH_3$, $OCF_3$ and $OCHF_2$.

24. The method as claimed in claim 1, where n is 1.

25. The method as claimed in claim 1, where $R^2$ is selected from the group consisting of F, Cl, CN and $CF_3$.

26. The method as claimed in claim 1, where m is 1, 2 or 3.

27. The method as claimed in claim 1, where the compound of formula V is a compound of formula V.1

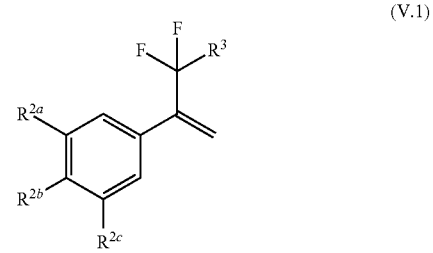

where $R^{2a}$, $R^{2b}$ and $R^{2c}$ are hydrogen or have one of the meanings given in claim 1 for $R^2$.

28. The method as claimed in claim 22, where
$R^{2a}$ is selected from the group consisting of H, F, Cl and $CF_3$;
$R^{2b}$ is selected from the group consisting of H, F, Cl and CN;
$R^{2c}$ is selected from the group consisting of H, F, Cl and $CF_3$.

29. The method as claimed in claim 1, where $R^3$ is selected from the group consisting of H, F, Cl and $CF_3$.

* * * * *